(12) United States Patent
Demmer et al.

(10) Patent No.: US 7,968,767 B2
(45) Date of Patent: Jun. 28, 2011

(54) ANTIFREEZE PROTEINS ISOLATED FROM FORAGE GRASSES AND METHODS FOR THEIR USE

(76) Inventors: Jeroen Demmer, Auckland (NZ); Steven Anthony Fish, Wales (GB); Claire Hall, Auckland (NZ); Michael Andrew Shenk, San Francisco, CA (US)

(*) Notice: Subject to any disclaimer, the term of this patent is extended or adjusted under 35 U.S.C. 154(b) by 965 days.

(21) Appl. No.: 11/594,324

(22) Filed: Nov. 7, 2006

(65) Prior Publication Data

US 2007/0113304 A1 May 17, 2007

Related U.S. Application Data

(63) Continuation-in-part of application No. 10/657,852, filed on Sep. 9, 2003, now Pat. No. 7,132,263.

(60) Provisional application No. 60/409,557, filed on Sep. 9, 2002.

(51) Int. Cl.
*A01H 1/00* (2006.01)
*C12N 15/29* (2006.01)
*C07H 21/04* (2006.01)
*C07K 14/415* (2006.01)

(52) U.S. Cl. ........... 800/289; 435/6; 435/69.1; 435/468; 435/419; 435/320.1; 530/370; 536/23.6; 800/278; 800/295

(58) Field of Classification Search .............. 435/6, 69.1, 435/468, 419, 320.1; 536/23.6; 800/278, 800/295, 289; 530/370
See application file for complete search history.

(56) References Cited

U.S. PATENT DOCUMENTS

2010/0192265 A1* 7/2010 Andersen et al. .......... 800/320.1
2010/0210597 A1* 8/2010 Moss et al. ...................... 514/81

FOREIGN PATENT DOCUMENTS

| WO | 98/04699 | 2/1998 |
| WO | 99/06565 | 2/1999 |
| WO | 99/37782 | 7/1999 |
| WO | 01/83534 A1 | 11/2001 |

OTHER PUBLICATIONS

Saren et al., EST Database, Acc. No. AJ460319, direct submission, May 24, 2002, see Result 12.*
Demmer et al., Issued_Patents_NA Database, US Pat. No. 7132263, Seq ID No. 4.*
Demer et al., Issued_Patents_NA Database, US Pat. No. 7132263, Seq ID No. 4, Nov. 7, 2006.*
Twigg, S., et al., "Frozen Food Product" EMBL/GenBank/DDBJ databases, (Jul. 1999) Accession No. AX019971.
Sidebottom, C.M., unknown, GenBank database, (Apr. 2000) Accession No. LPE277399.
Sidebottom, C.M., unknown, GenBank database, (Apr. 2000) Accession No. CAB87814.
Strom. et al., J Am Chem Soc. 127(1):428-440. 2005.
Strom. et al., Biol Chem. 279(1):32407-417.2004.
Ngo in, "The Protein Folding Problem and Tertiary Structure Prediction." MERZ et al. (eds.), Birkhauser Bostyon: Boston, MA, pp. 433 and 492-495, 1994.
Rudinger in "Peptide Hormones." Parsons (ed.), University Park Press, Baltimore, MD, pp. 1-7, 1976.
Davies et al. "Structure and Function of Antifreeze Proteins." Phil. Trans. R. Soc., London, 357(1423): 927-35, 2002.

* cited by examiner

*Primary Examiner* — Phuong T Bui
(74) *Attorney, Agent, or Firm* — Janet Sleath; Speckman Law Group PLLC

(57) ABSTRACT

Isolated polynucleotides encoding antifreeze polypeptides are provided, together with expression vectors and host cells comprising such isolated polynucleotides. Methods for the use of such polynucleotides and polypeptides are also provided.

14 Claims, 11 Drawing Sheets

Figure 1

```
MAKCWQLLLFLALLLPAASAASCHPDDLYALRDFAGNLRGGGVLLRAALPGASCCGWEGV      60
GCDGASGCVKSFQILLKGLTAAGRSLGKAFTHMPLHVKPSQGTLDEDHNTITGINNTVRS     120
GSNNVVSGNDNTVISGNNNVVSGSHNTVVFGGDNFISGSYHVVSGNHHVVTDNKNAVSGD     180
HNTVSGSQNTVSGNHQIVSGSHSTVSGNHNTVSGRNNSVYGNNNIVSGSNHVVYGNNKVV     240
TGG                                                              243
```

Figure 2

```
MAKCWQLLLFLAFLLPAASAASRHPDDLRALQDFAGNLRGGGVVLRAALSGGSCCDWEGA      60
GCDGASGRVTSFQILLKGLTTAGRSLGKAFTNMPLHVKSSQGTLDEEHNTITGINNTVKS    120
GSNNVVSGNDNTVISGNNNVVSGSHNTVVFGGDNFLSGSNHVVSGNHHVVTDNKNAVSGD    180
HNTVSGSQNTVSGNHHIISASHSTISGNHNTVSGSNNFVSGNNNIVSGSNHVVYGNNKVV    240
TGG                                                              243
```

Figure 3

```
MPEYMAKCCMLLVFLGFILQVAGATSWSCHHDDLHALRGLAENLSGKGAVRLRAAWSGAS     60
CCSWEGVGCETASGRVVALRLPKRGLGGIIPSSIGELDHLRYLDLSGNSLVGEVPKSLQI    120
RLKSLTTDSQSLGMGSINMLLHVSSRRTLDEEPNTISGTNNSVGSGSNNVVSGNDNTVVS    180
GNNHVSGSNNTVVTGSDNTVVGSNHVVSGTKHIVTDNNNVVSGNDNNVSGSFHTVSGEH    240
NTVSGSNNTVSGSNHIVSGSNKVVTDG                                      267
```

Figure 4

MPEYMAKCCMLLLLLAFILLQVAGATSWSCHHDDLRALRGFAENLSGKGAVRLRAAWSGA          60

SCCSWEGVGCETASGRVAALRLPKRGLGGTIPSSIGELDHLRCLDLSGNSLVGKVPKSLQ          120

IRLXSLSTDGQSLGMGSINTLLHVSSNRRTLDEEPNTISGTNNSVGSGSNNVVSGNDNTV          180

ISGNNNHVSGSNNTVVTGSDNTLVGSNHVVSGTKHIVTDNNNVVSGNDNNVSGSFHTVSG          240

EHNTVSGSNNTVSGSNHVVSGSNKVVTDG                                        269

Figure 5

MAKCWLLLL*FLVFLLLAMSATS*CHLDDLRALRGFVGNLNGGGALLRGTWSGSSCCDWEGV         60

GCDGTSGRVTALRLPISLEDCGKLKSLNLANERLVGTIPSWIGELDHHCYLVLSDNSLVG         120

KAPNSLHNSLQIRLKGLATAGRSLGMAFANMPLHVKGNRRTLDEQTNTIHGTNNTVRSGN         180

DNAVSGNDNTVICGNNNTVSGSNNTIASGSDNIVTGSNHIVCGTKHIITDNNNDVSGNDN         240

NVSGSFHTVSGSHNTVSGSNNTVSGSNHVVSGSNKLVTGDE                           281

Figure 6

MAKCWLLLLFLV*VLLPAASATS*CHPDDLRALRGFVGNLNGGGVLLHGAWSGSLCCAWEGV         60

GCDGTSGRVTALRLPISLKDCGKLKSLNLANDRLVGTIPSWIGELDHLCYLVLSDNSLVG         120

KVPNSLQIRLKGLATAGRSLGMAFANMPLHVKGNRRTLDEQTNTIQGTNNTVRSGNDAV         180

SGNDNTVICGNNNTVSGSNNTIVSGSDNIVTGSNQVVCGTKHIITDNNNDVSGNDNNVSG         240

SSHTVSGSHNTVSGSNNTVSGSNHVVSGSNKVVTGDE                               277

Figure 7

MAKCWLLLLFLVFLLLAV<u>C</u>ATS<u>C</u>HPDDLRALRGFVGNLNGGGVLLRETWSGS<u>SCCAWEGV</u>   60

<u>GCDGTSGRVTALRLPISLEDCGKLKSLNLANERLVGTIPSWIGELDHHCYFVLSDNSLVG</u>   120

<u>KVPNS</u>LQIRLKGLATAGRSLGMAFANMPLHVKGNRRTLDE QTNTIHGTNNTVRSGNDNAV   180

SGNDNTVMCGNNNTVSGSNNTISSGSDNIVTGSNHIVCGTKHIITDNNNDVSGNDNNVSG   240

SFHTVSGSHNTVSGSNNTVSGSNHVVSGSNKVVTG DE   277

Figure 8

MGLLLLFLAFL<u>LPVACAATSS</u>CHPDDLRALRGFAKNLGGGGVLLRTAWSGT<u>SCCVWEGVG</u>   60

<u>CNG</u>ASGR<u>VTTLWLPRRGLAGTITGASLAGLARLESLNLANNRLVGTIPSWIGELDHLLYL</u>   120

<u>DLSHNSLVGELPNL</u>KGLTTTGHLLGMAFTSMPLDVKPNRRTLAV QPNTISGTNNSVLSGR   180

NNTVSGNDNTVISGNNNTVSGSFNTVVTGSDNVLTGSNHVVSGRNHIVTDNNNAVSGDDN   240

NVSGSFHKVSGSHNTVSGSNNTVSGRNHVVSGSNKVVTG G   280

Figure 9

MGLLLLFLGFL<u>LPAACAATSS</u>CHPDDLRALRGFAKNVGGGGVLLRTAWSGT<u>SCCVWEGVG</u>   60

<u>CNG</u>ASGR<u>ITTLWLPRRGLAGTITGASLAGLARLESLNLANNRLVGTIPSWIGELDHLLYL</u>   120

<u>DLSHNSLVGELPNR</u>LQIR<u>LKGLTTTGHLLGMAFTNMPLDVKRNRRTLAI</u> QPNTISGTNNL   180

VLSGRNNVVSGNDNTVISENNNTVSGSFNTVITGSDNVLTGSNHVVSGRSHIVTDNNNSV   240

SGDDNNVSGSFHKVSGSHNTVSGSNNTVSGRNHVVSGSNKIVTG G   285

Figure 10

| | |
|---|---|
| MAKCLMLLLSFAFLLSVAGTATATPCHRDDLRALRGFAENLGGGGAISLRAAWSGASCCD | 60 |
| WEGVGCDGASGRVTALWLPRSGLTGPIPSWICQLHHLRYLDLSGNALVGEVPKNLQVQLK | 120 |
| GITNMPLHVMRNRRSLDEQPNTISGSNNTVRSGSKNVLAGNDNTVISGDNNSVSGSNNTV | 180 |
| VSGNDNTVTGSNHVVSGTNHIVTDNNNNVSGNDNNVSGSFHTVSGGHNTVSGSNNTVSGS | 240 |
| NHVVSGSNKVVTDA | 254 |

Figure 11

| | |
|---|---|
| MAKCLMLLLSFAFLLSAAGTATATPCHRDDLRALRGFAENLGGGGALSLRAAWSGASCCD | 60 |
| WEGVGCDGASGRVTALWLPRSGLTGPIPSWICQLHHLRYLDLSGNALVGEVPKNLQVQLK | 120 |
| GLTAAGRSGFTNMPLHVMRNRRSLDEQPNTISGSNNTVRSGSKNVVAGNDNTVISGDNNS | 180 |
| VSGSNNTVVSGSDNTVTGSNHVVSGTNHIVTDNNNNVSGNDNNVSGSFHTVSGGHNTVSG | 240 |
| SNNTVSGSNHVVSGSNKVVTDA | 262 |

Figure 12

| | |
|---|---|
| MAKCLMLLLSFAFLLSAAGTATATATPCHRDDLRALRGFAENLGGGGALSLRAAWSGASC | 60 |
| CDWEGVGCDGASGRVTALWLPRSGLTGPIPSWIFQLHHLRYLDLSGNALVGEVPKNLQVQ | 120 |
| LKGITNMPLHVMRNRRSLDEQPNTISGSNNTVRSGSKNVLAGNDNTVISGDNNSVSGSNN | 180 |
| TVVSGNDNTVTGSNHVVSGTNHIVTDNNNNVSGNDNNVSGSFHTVSGGHNTVSGSNNTVS | 240 |
| GSNHVVSGSNKVVTDA | 256 |

Figure 13

MAKCWLLLL*FLVFLLLAMSATS*CHLDDLRALRGFVGNLNGGGALLRGTWSGS<u>SCCDWEGV</u>  60

<u>GCDG</u>TSGRVTALRLPISLEDCGKLKSLNLANERLVGTIPSWIGELDHHCYLVLSDNSLVG  120

KAPNSLHNSLQIRLKGLATAGRSLGMAFANMPLHVKGNRRTLDE QTNTIHGTNNTVRSGN  180

DNAVSGNDNTVICGNNNTVSGSNNTIASGSDNIVTGSNHIVCGTKHIITDNNNDVSGNDN  240

NVSGSFHTVSGSHNTVSGSNNTVSGSNHVVSGSNKVVTG DE  281

ANTIFREEZE PROTEINS ISOLATED FROM FORAGE GRASSES AND METHODS FOR THEIR USE

REFERENCE TO RELATED APPLICATIONS

This application is a continuation-in-part of U.S. patent application Ser. No. 10/657,852, filed Sep. 9, 2003, now U.S. Pat. 7,132,263, which claims priority to U.S. Provisional Patent Application No. 60/409,557, filed Sep. 9, 2002.

TECHNICAL FIELD OF THE INVENTION

This invention relates to polynucleotides isolated from forage grass tissues, specifically from *Lolium perenne* (perennial ryegrass) and *Festuca arundinacea* (tall fescue), as well as oligonucleotide probes and primers, genetic constructs comprising the polynucleotides, biological materials (including host cells and plants) incorporating the polynucleotides, polypeptides encoded by the polynucleotides, and methods for using the polynucleotides and polypeptides. More particularly, the invention relates to antifreeze polypeptides involved in ice recrystallization pathways, and to polynucleotides encoding such polypeptides that confer freezing tolerance to plants.

BACKGROUND OF THE INVENTION

Many organisms that inhabit environments where they are repeatedly exposed to freezing conditions have evolved specific antifreeze proteins (AFPs) that provide both freeze resistance and freeze tolerance (for review see Jia and Davies *Trends in Biochemical Science* 27:101-106, 2002). Significant potential exists to improve the survival of organisms, such as plants, by enhancing the expression of antifreeze proteins or by introducing antifreeze proteins into organisms that are currently freeze-intolerant. Such methods would, for example, extend the range of climates in which forage crops and other commercially useful plants could be produced. Such methodology could also be applied to microorganisms in order to increase survival during recovery from cold temperatures, or may be employed in a similar fashion to improve survivability associated with temperature fluctuations which occur during transportation at low temperatures.

Antifreeze proteins are found in a wide range of organisms including plants, fish, insects and bacteria. Although all AFPs are ice-binding proteins, there is a large variation in structure and amino acid sequence between organisms. For example, the AFPs from fish are very different from those of plants. Even within different plant species there is little amino acid sequence homology between known AFP proteins, indicating that AFPs have evolved separately in a number of plant species. This structural diversity has made it difficult to identify functional domains in the AFP proteins, as well as to identify residues involved in the ice-protein interaction.

It has been proposed that AFPs bind to ice as a receptor-ligand interaction, with ice and AFPs being the ligand and receptor, respectively, to prevent further growth of the crystals. In certain freeze tolerant organisms, such as plants, the ice forms in the extra-cellular space. At several degrees below the melting point there is a tendency for ice to re-crystallize, with large crystals forming at the expense of smaller ones. These large crystals have the ability to irreparably damage cells. The main role of AFPs is therefore to slow or halt this re-crystallization process. Plant AFPs in particular tend to be good at inhibiting the ice re-crystallization process thereby lessening the damage caused by freezing. This contrasts with AFPs of Antarctic marine fish, which have an additional thermal hysteresis (TH) activity that reduces the freezing temperature of water inside the fish by controlling ice crystal growth.

Plant AFPs have been isolated from rye, perennial ryegrass and carrot. The carrot protein contains leucine-rich repeats and has some similarity with polygalacturonase inhibitor proteins (Worrall et al., *Science* 282:115-117, 1998; Smallwood et al., *Biochem. J* 340:385-391, 1999). Over-expression of the carrot antifreeze protein in transgenic tobacco plants resulted in accumulation of this AFP in the apoplast. In ice re-crystallization experiments, the carrot protein inhibited the size of ice crystals formed. The TH activity of the carrot AFP was low; between 0.2 to 0.6° C.

The perennial ryegrass AFP is rich in asparagine, valine and glycine residues and shares no sequence homology to the carrot AFP (WO 99/37782, Sidebottom et al., *Nature* 406: 256, 2000). The grass AFP has ice re-crystallization activity similar to that observed for the carrot AFP and has a low TH (0.2-0.45° C.). A theoretical three-dimensional structure has been developed for the grass AFP protein showing that it has a β-roll conformation (Kuiper et al., *Biophys. J.* 81:3560-3565, 2001). This gives the protein a long flat structure and presents two large flat surfaces for ice-binding. The physicochemical characteristics of an AFP derived from *Lolium* have recently been investigated (Pudney et al., *Archiv. Biochem. Biophys.* 410:238-245, 2003).

The scope for AFP applications extends from genetically modifying prokaryotic or eukaryotic organisms to produce formerly non-resident AFP proteins, into areas where AFPs are used as additives for cryoprotection. An example of this is molecular biology reagents such as restriction endonucleases, DNA modifying enzymes, DNA polymerases and associated buffers which are sensitive to freeze thaw. Molecular biology reagents which are particularly sensitive to freezing, such as in vitro transcription/translation systems could potentially benefit by the presence of AFPs. Whole cells, such as preparations of *Escherichia coli*, yeasts, blood platelets, red blood cells, ova and sperm, in addition to multicelluar complexes such as embryos and whole organs, could be protected by the ice restructuring properties of AFPs.

AFPs may also be usefully employed in frozen food products where small crystalline structure is desirable, such as ice cream, and to provide a superior food quality upon thawing of frozen food products such as frozen fruit. For example, International Patent Publication WO 92/22581 describes the use of plant AFPs in controlling ice crystal shape in ice cream. International Patent Publication WO 99/37782 describes the isolation of AFPs from grasses and the use of such AFPs in frozen food products, such as ice cream and frozen yogurt. A particularly attractive trait, which is exhibited by *Lolium* AFPs, is their stability at high temperature (Pudney et al., *Archiv. Biochem. Biophys* 410:238-245, 2003). This lends itself to applications within the food industry where high temperature treatments, such as pasteurization, are routinely used to inhibit microbial proliferation. AFPs may also be used in meat products to preserve texture and flavor after cold storage.

The ability to alter ice recrystallization may have wider applications within industrial crystallization processes. One example is separation, purification and consistency in the production of pharmaceuticals, agrochemicals and pigments. AFPs could also be employed in the sugar industry where controlling crystal formation is highly desirable.

Another area where the manipulation of crystal architecture is desirable is in healthcare. AFPs could be localized in tumours where their propensity to form hexagonal bipyramids would facilitate cellular damage. This type of treatment is particularly attractive because it is minimally invasive and does not have the accompanying negative side effects associated with traditional chemotherapy. Other healthcare applications include controlling the formation of biocrystals in disorders such as gout and in kidney stones.

It has been postulated that AFPs affect crystal formation by interfering with the molecular interactions between water molecules, see Jia and Davies, *Trends in Biochemical Science* 27:101-106, 2002. This could be used to assist the drying of, for example, dairy products or pharmaceuticals where a major component of process costs is incurred as part of the drying process.

SUMMARY OF THE INVENTION

The present invention provides antifreeze proteins that are encoded by polynucleotides isolated from forage grass tissues. The polynucleotides were isolated from *Lolium perenne* (perennial ryegrass) and *Festuca arundinacea* (tall fescue) tissues taken at different times of the year, specifically in winter and spring, and from different parts of the plants, including: leaf blades, leaf base, pseudostems, roots and stems. The present invention also provides genetic constructs, expression vectors and host cells comprising the inventive polynucleotides, and methods for using the polynucleotides and genetic constructs to modulate the cold tolerance of organisms, such as plants.

In specific embodiments, the isolated polynucleotides disclosed herein comprise a sequence selected from the group consisting of: (a) SEQ ID NO: 1-12 and 25; (b) complements of SEQ ID NO: 1-12 and 25; (c) reverse complements of SEQ ID NO: 1-12 and 25; (d) reverse sequences of SEQ ID NO: 1-12 and 25; (e) sequences having a 99% probability of being functionally or evolutionarily related to a sequence of (a)-(d), determined as described below; and (f) sequences having at least 75%, 80%, 90%, 95% or 98% identity to a sequence of (a)-(d), the percentage identity being determined as described below. Polynucleotides comprising at least a specified number of contiguous residues ("x-mers") of any of SEQ ID NO: 1-12 and 25; and oligonucleotide probes and primers corresponding to SEQ ID NO: 1-12 and 25 are also provided. All of the above polynucleotides are referred to herein as "polynucleotides of the present invention."

In further aspects, isolated polypeptides encoded by the polynucleotides disclosed herein are provided. In specific embodiments, such polypeptides comprise an amino acid sequence of SEQ ID NO: 13-24 and 26. Polypeptides comprising a sequence having at least 75%, 80%, 90%, 95% or 98% identity to a sequence of SEQ ID NO: 13-24 and 26, wherein the polypeptide possesses the same functional activity as the polypeptide comprising a sequence of SEQ ID NO: 13-24 and 26 are also provided. The present invention further contemplates isolated polypeptides comprising at least a functional portion of a polypeptide comprising an amino acid sequence selected from the group consisting of: (a) SEQ ID NO: 13-24 and 26; and (b) sequences having at least 75%, 80%, 90%, 95% or 98% identity to a sequence of SEQ ID NO: 13-24 and 26.

In another aspect, genetic constructs comprising a polynucleotide of the present invention, either alone or in combination with one or more of the inventive sequences, or in combination with one or more known polynucleotides are provided.

In addition, methods for the production of polypeptides derived from the inventive polynucleotides such that monomeric or multimeric forms of the same or different polypeptides are generated, are provided. This type of construct has been identified as offering enhanced activity, see Baardnes et al., *J. Biol. Chem.* in press, 2003, Miura et al., *J. Biol. Chem.* 276: 1304-1310, 2001, and Nishimiya et al., *J. Biol. Chem.* 278:32307-32312, 2003.

In certain embodiments, genetic constructs are provided that comprise, in the 5'-3' direction: a gene promoter sequence; an open reading frame coding for at least a functional portion of a polypeptide disclosed herein; and a gene termination sequence. An open reading frame may be orientated in either a sense or anti-sense direction. Genetic constructs comprising a non-coding region of a polynucleotide disclosed herein or a polynucleotide complementary to a non-coding region, together with a gene promoter sequence and a gene termination sequence, are also provided. Preferably, the gene promoter and termination sequences are functional in a host cell, such as a plant cell. Most preferably, the gene promoter and termination sequences are those of the original enzyme genes but others generally used in the art, such as the Cauliflower Mosaic Virus (CMV) promoter, with or without enhancers, such as the Kozak sequence or Omega enhancer, and *Agrobacterium tumefaciens* nopalin synthase terminator may be usefully employed. Tissue-specific promoters may be employed in order to target expression to one or more desired tissues. The construct may further include a marker for the identification of transformed cells.

In a further aspect, transgenic cells, such as transgenic plant cells, comprising the constructs of the present invention are provided, together with tissues and plants comprising such transgenic cells, and fruits, seeds and other products, derivatives, or progeny of such plants.

In yet another aspect, methods for modulating the cold tolerance of a target organism, such as a plant, are provided, such methods including stably incorporating into the genome of the target organism a genetic construct comprising a polynucleotide of the present invention. In a preferred embodiment, the target organism is a plant, preferably selected from the group consisting of commercially important trees and crop plants.

In a related aspect, a method for producing an organism or cell line, for example a prokaryotic or eukaryotic organism or cell line, such as a bacterium, yeast, mammalian cell line or plant, having increased cold tolerance is provided, the method comprising transforming a cell with a genetic construct comprising of the present invention to provide a transgenic cell, and cultivating the transgenic cell under conditions conducive to regeneration and mature growth.

In yet a further aspect, methods are provided for modifying the activity of an antifreeze protein in a target organism, such as a plant, comprising stably incorporating into the genome of the target organism a genetic construct disclosed herein.

Methods of cryopreserving cells, tissues or organisms are further provided, such methods comprising contacting the cell, tissue or organism to be preserved with a polypeptide disclosed herein. Such cells, tissues and organisms may be selected, for example, from the group consisting of: mammals, plants, insects, fungi and bacteria.

In related applications, molecular biology reagents, such as buffers, enzymes and in vitro protein synthesis systems, containing a polypeptide disclosed herein are provided. Food additives comprising a polypeptide disclosed herein are also provided, together with frozen food products comprising such food additives. In certain embodiments, such frozen food products are selected from the group consisting of: frozen fruit, frozen vegetables, ice cream, frozen yogurt, sherbet, sorbet, ice milk, water-ices, granites, frozen fruit purees and frozen meats. Preferably the amount of the inventive AFP within such products is from 0.00001 to 0.5%, by weight.

In another aspect, the disclosed polypeptides may be employed as additives in industrial crystallization processes used in the separation and/or purification of compounds, or as components to improve consistency, for example, in pharmaceutical or agrochemical pigment production, or in the production of sugar and other crystalline materials. The polypeptides disclosed herein may thus be usefully employed in conjunction with known processes for the crystallization of sugar, such as those described in U.S. Pat. Nos. 4,216,025 and 5,286,298, and known processes for the production of pharmaceuticals, agrochemicals and pigments, such as that described in U.S. Pat. No. 6,506,886. The ability of polypeptides disclosed herein to directly impact crystal formation in sucrose solutions has been demonstrated in a SPLAT ice-recrystallization assay, as described below in Example 3.

The polypeptides disclosed herein may also be employed in therapeutic agents for the inhibition, disruption and/or restructuring of the crystal architecture within biocrystals associated with disorders such as gout and kidney stones. The inventive polypeptides may also be introduced into unwanted tissue, such as tumors to promote cellular damage upon freezing when accompanied by a localized application of low temperature on or around the tumor site, as detailed, for example, in U.S. Pat. No. 5,654,279.

In addition, the inventive polypeptides may be employed in industrial or manufacturing processes to accelerate drying, such as in the production of foodstuffs such as milk, and in the pharmaceutical industry where various drying technologies are used, for example freeze-drying and spray drying.

BRIEF DESCRIPTION OF THE DRAWINGS

FIG. 1 shows the amino acid sequence of SEQ ID NO: 13, a *Lolium perenne* antifreeze protein. The signal sequence is underlined, and the 7-amino acid sequence repeat region identified in antifreeze proteins (Sidebottom et al., *Nature* 406:256, 2000; Kuiper et al., *Biophys. J.* 81:3560-3565, 2001) is boxed. A conserved lipoprotein membrane attachment site is in bold and italics, and conserved Cys-pairs identified N-terminal of leucine-rich repeats of receptor-like kinases (Van der Knaap et al., *Plant Physiol.* 120:559-569, 1999) are double underlined.

FIG. 2 shows the amino acid sequence of SEQ ID NO: 14, a *Festuca arundinacea* antifreeze protein homolog. The signal sequence is underlined, the 7-amino acid sequence repeat region identified in antifreeze proteins (Sidebottom et al., *Nature* 406:256, 2000; Kuiper et al., *Biophys. J.* 81:3560-3565, 2001) is boxed and conserved Cys-pairs identified N-terminal of leucine-rich repeats of receptor-like kinases (Van der Knaap et al., *Plant Physiol.* 120:559-569, 1999) are double underlined.

FIG. 3 shows the amino acid sequence of SEQ ID NO: 15, a *Lolium perenne* antifreeze protein homolog. The signal sequence is underlined, and the 7-amino acid sequence repeat region identified in antifreeze proteins (Sidebottom et al., *Nature* 406:256, 2000; Kuiper et al., *Biophys. J* 81:3560-3565, 2001) is boxed. Conserved leucine-rich repeats are in bold and underlined (Worrall et al., *Science* 282:115-117, 1998) and cysteine-pairs with the conserved amino acid sequence of cysteine pairs found N-terminal of leucine-rich repeats of receptor-like kinases (Van der Knaap et al., *Plant Physiol.* 120:559-569, 1999) are double underlined.

FIG. 4 shows the amino acid sequence of SEQ ID NO: 16, a *Festuca arundinacea* antifreeze protein homolog. The signal sequence is underlined, and the 7-amino acid sequence repeat region identified in antifreeze proteins (Sidebottom et al., *Nature* 406:256, 2000; Kuiper et al., *Biophys. J.* 81:3560-3565, 2001) is boxed. Conserved leucine-rich repeats are in bold and underlined (Worrall et al., *Science* 282:115-117, 1998) and cysteine-pairs with the conserved amino acid sequence of cysteine pairs found N-terminal of leucine-rich repeats of receptor-like kinases (Van der Knaap et al., *Plant Physiol.* 120:559-569, 1999) are double underlined.

FIG. 5 shows the amino acid sequence of SEQ ID NO: 17, a *Lolium perenne* antifreeze protein homolog. The signal sequence is underlined, the 7-amino acid sequence repeat region identified in antifreeze proteins (Sidebottom et al., *Nature* 406:256, 2000; Kuiper et al., *Biophys. J.* 81:3560-3565, 2001) is boxed and a conserved lipoprotein membrane attachment site is in bold and italics. Conserved leucine-rich repeats are in bold and underlined (Worrall et al., *Science* 282:115-117, 1998) and cysteine-pairs with the conserved amino acid sequence of cysteine pairs found N-terminal of leucine-rich repeats of receptor-like kinases (Van der Knaap et al., *Plant Physiol.* 120:559-569, 1999) are double underlined.

FIG. 6 shows the amino acid sequence of SEQ ID NO: 18, a *Festuca arundinacea* antifreeze protein homolog. The signal sequence is underlined, and the 7-amino acid sequence repeat region identified in antifreeze proteins (Sidebottom et al., *Nature* 406:256, 2000; Kuiper et al., *Biophys. J.* 81:3560-3565, 2001) is boxed and a conserved lipoprotein membrane attachment site is in bold and italics. Conserved leucine-rich repeats are in bold and underlined (Worrall et al., *Science* 282:115-117, 1998) and cysteine-pairs with the conserved amino acid sequence of cysteine pairs found N-terminal of leucine-rich repeats of receptor-like kinases (Van der Knaap et al., *Plant Physiol.* 120:559-569, 1999) are double underlined.

FIG. 7 shows the amino acid sequence of SEQ ID NO: 19, a *Lolium perenne* antifreeze protein homolog. The signal sequence is underlined, and the 7-amino acid sequence repeat region identified in antifreeze proteins (Sidebottom et al., *Nature* 406:256, 2000; Kuiper et al., *Biophys. J.* 81:3560-3565, 2001) is boxed. Conserved leucine-rich repeats are in bold and underlined (Worrall et al., *Science* 282:115-117, 1998) and cysteine-pairs with the conserved amino acid sequence of cysteine pairs found N-terminal of leucine-rich repeats of receptor-like kinases (Van der Knaap et al., *Plant Physiol.* 120:559-569, 1999) are double underlined.

FIG. 8 shows the amino acid sequence of SEQ ID NO: 20, a *Lolium perenne* antifreeze protein homolog. The signal sequence and transmembrane domain are underlined, and the 7-amino acid sequence repeat region identified in antifreeze proteins (Sidebottom et al., *Nature* 406:256, 2000; Kuiper et al., *Biophys. J.* 81:3560-3565, 2001) is boxed. A conserved lipoprotein membrane attachment site is in bold and italics. Conserved leucine-rich repeats are in bold and underlined (Worrall et al., *Science* 282:115-117, 1998) and cysteine-pairs with the conserved amino acid sequence of cysteine pairs found N-terminal of leucine-rich repeats of receptor-like kinases (Van der Knaap et al., *Plant Physiol.* 120:559-569, 1999) are double underlined.

FIG. 9 shows the amino acid sequence of SEQ ID NO: 21, a *Festuca arundinacea* antifreeze protein homolog. The signal sequence and transmembrane domain are underlined, and the 7-amino acid sequence repeat region identified in antifreeze proteins (Sidebottom et al., *Nature* 406:256, 2000; Kuiper et al., *Biophys. J.* 81:3560-3565, 2001) is boxed. Conserved leucine-rich repeats are in bold and underlined (Worrall et al., *Science* 282:115-117, 1998) and cysteine-pairs with the conserved amino acid sequence of cysteine pairs found N-terminal of leucine-rich repeats of receptor-like kinases (Van der Knaap et al., *Plant Physiol.* 120:559-569, 1999) are double underlined. A conserved lipoprotein membrane attachment site is in bold and italics.

FIG. 10 shows the amino acid sequence of SEQ ID NO: 22, a *Lolium perenne* antifreeze protein homolog. The signal sequence is underlined, and the 7-amino acid sequence repeat region identified in antifreeze proteins (Sidebottom et al., *Nature* 406:256, 2000; Kuiper et al., *Biophys. J.* 81:3560-3565, 2001) is boxed. Conserved leucine-rich repeats are in bold and underlined (Worrall et al., *Science* 282:115-117, 1998) and cysteine-pairs with the conserved amino acid sequence of cysteine pairs found N-terminal of leucine-rich repeats of receptor-like kinases (Van der Knaap et al., *Plant Physiol.* 120:559-569, 1999) are double underlined.

FIG. 11 shows the amino acid sequence of SEQ ID NO: 23, a *Festuca arundinacea* antifreeze protein homolog. The signal sequence is underlined, and the 7-amino acid sequence repeat region identified in antifreeze proteins (Sidebottom et al., *Nature* 406:256, 2000; Kuiper et al., *Biophys. J.* 81:3560-3565, 2001) is boxed. Conserved leucine-rich repeats are in bold and underlined (Worrall et al., *Science* 282:115-117, 1998) and cysteine-pairs with the conserved amino acid sequence of cysteine pairs found N-terminal of leucine-rich repeats of receptor-like kinases (Van der Knaap et al., *Plant Physiol.* 120:559-569, 1999) are double underlined.

FIG. 12 shows the amino acid sequence of SEQ ID NO: 24, a *Lolium perenne* antifreeze protein homolog. The signal sequence is underlined, and the 7-amino acid sequence repeat region identified in antifreeze proteins (Sidebottom et al., *Nature* 406:256, 2000; Kuiper et al., *Biophys. J.* 81:3560-3565, 2001) is boxed. Conserved leucine-rich repeats are in bold and underlined (Worrall et al., *Science* 282:115-117, 1998) and cysteine-pairs with the conserved amino acid sequence of cysteine pairs found N-terminal of leucine-rich repeats of receptor-like kinases (Van der Knaap et al., *Plant Physiol.* 120:559-569, 1999) are double underlined.

FIG. 13 shows the amino acid sequence of SEQ ID NO: 26, a *Lolium perenne* antifreeze protein homolog. The signal sequence is underlined, and the 7-amino acid sequence repeat region identified in antifreeze proteins (Sidebottom et al., *Nature* 406:256, 2000; Kuiper et al., *Biophys. J.* 81:3560-3565, 2001) is boxed. Conserved leucine-rich repeats are in bold and underlined (Worrall et al., *Science* 282:115-117, 1998) and cysteine-pairs with the conserved amino acid sequence of cysteine pairs found N-terminal of leucine-rich repeats of receptor-like kinases (Van der Knaap et al., *Plant Physiol.* 120:559-569, 1999) are double underlined.

DETAILED DESCRIPTION OF THE INVENTION

Figure 14:
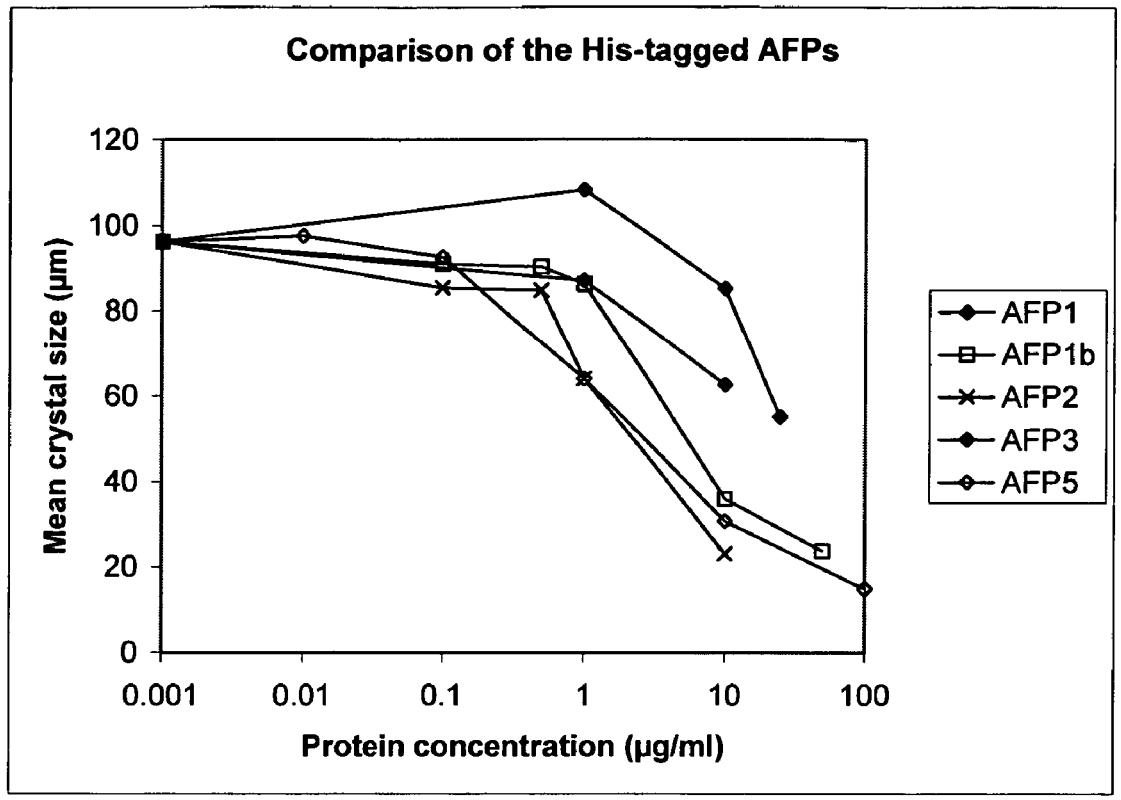
FIG. 14 shows ice re-crystallization inhibition activity of His-tagged AFP1, AFP1b, AFP2, AFP3 and AFP5, determined by measuring crystal size after 30 minutes at −8° C. Protein concentrations are shown on a log scale.

The polypeptides disclosed herein, and the polynucleotides encoding the polypeptides, have activity in cold tolerance and anti-freeze pathways in plants. Using the methods and materials disclosed herein, the cold tolerance of a plant may be modulated by modulating expression of polynucleotides of the present invention, or by modifying the polynucleotides or the polypeptides encoded by such polynucleotides. The isolated polynucleotides and polypeptides disclosed herein may thus be usefully employed in improving cold tolerance in any plant, thereby improving its performance and extending the range of climates in which it may be grown.

The cold tolerance of an organism, such as a plant, may be modified by incorporating additional copies of polynucleotides encoding the disclosed anti-freeze proteins into the genome of the target organism. In addition, cold or freezing tolerance of mammalian, plant, insect, bacteria, archaea and fungal cells or tissues may be modified by incorporating additional copies of the disclosed polynucleotides into the genome of the cells or tissues. The polynucleotides introduced may be in monomeric or multimeric form, composed of repeat units of the same specified polynucleotide or in combination with any of the other inventive polynucleotide sequences. The polypeptides encoded by the disclosed anti-freeze protein polynucleotides can also be usefully employed in the cryopreservation of mammalian, plant, insect, bacteria, archaea and fungal cells or tissues.

Plant AFPs have demonstrated ice restructuring activity (Hon et al., *Plant Physiol.* 109:879-889, 1995; Sidebottom et al., *Nature* 406:256, 2000 and Pudney et al., *Arch. Biochem. Biophys.* 410:238-245, 2003), which can be enhanced by generating multimeric forms, see Baardnes et al., *J. Biol. Chem.* in press, 2003, and Nishimiya et al., *J. Biol. Chem.* 278:32307-32312, 2003. The polypeptides disclosed herein, used either individually, in multiples thereof or as engineered polypeptides consisting of individual or multiple units of the same or different polypeptides, may be employed to modify crystallization processes. Applications within healthcare relate to cryosurgery, as described, for example, in U.S. Pat. No. 5,654,279 and the modification of biocrystals such as those associated with gout and kidney stones. In food, the disclosed polypeptides have applications in maintaining flavor and texture, by offsetting the damage caused by the formation of large ice crystals. Their ability to change the structure of ice cream, for example, permits a lower level of fat incorporation while maintaining a desirable consistency. This has the health benefits of reducing fat content and therefore generating a product with a lower calorific value per gram weight.

Alternatively the polypeptides disclosed herein, used either individually, in multiples thereof or as engineered polypeptides consisting of individual or multiple units of the same or different polypeptides, may be usefully employed in manufacturing processes which use a crystallization process to purify, separate, or maintain consistency, by controlling the size and/or rate of crystal formation. This has useful application in the pharmaceutical, agrochemical and pigment industries, and may also be employed in the food industry where the propagation of regular crystals is desirable, for example in the production of sugar.

Jia and Davies (*Trends in Biochemical Science* 27:101-106, 2002) have indicated that AFP mechanisms involve hydrogen, Van der Waals and hydrophobic interactions. As demonstrated below, the polypeptides disclosed herein, used either individually, in multiples thereof or as engineered polypeptides consisting of individual or multiple units of the same or different polypeptides, may be employed in drying processes to increase the rate of dehydration.

In one aspect, methods are provided for modulating the cold tolerance of an organism, such methods involving stably incorporating into the genome of the organism a genetic construct comprising one or more polynucleotides disclosed herein. In related aspects, methods for producing an organism having an altered genotype or phenotype is provided, such methods comprising transforming a cell with a genetic construct disclosed herein to provide a transgenic cell, and cultivating the transgenic cell under conditions conducive to regeneration and mature growth. Organisms, such as plants, having an altered genotype or phenotype as a consequence of modulation of the level or content of a polynucleotide or polypeptide disclosed herein compared to a wild-type organism, as well as components (seeds, etc.) of such organisms, and the progeny of such organisms, are contemplated by and encompassed within the present invention.

Target cells which may be usefully transformed with the genetic constructs disclosed herein include plant, mammalian, insert, fungal, archaea and bacterial cells. In one embodiment, the target organism is a plant species, preferably a cold sensitive plant, such as a cold sensitive tree or cold sensitive crop plant. Examples of cold sensitive trees include eucalyptus species. Examples of cold sensitive crop plants include rice, sugarcane and tropical fruit and vegetable plants. Other plants that may be usefully transformed with the disclosed genetic constructs include herbs, ornamental shrubs and flowering plants.

Additionally, the polynucleotide sequences identified as SEQ ID NO: 1-12 and 25 and their variants, may be used to design oligonucleotide probes and primers. Oligonucleotide probes and primers have sequences that are substantially complementary to the polynucleotide of interest over a certain portion of the polynucleotide. Oligonucleotide probes designed using the polynucleotides disclosed herein may be employed to detect the presence and examine the expression patterns of genes in any organism having sufficiently similar DNA and RNA sequences in their cells using techniques that are well known in the art, such as slot blot DNA hybridization techniques. Oligonucleotide primers designed using the polynucleotides disclosed herein may be used for PCR amplifications. Oligonucleotide probes and primers designed using such polynucleotides may also be used in connection with various microarray technologies, including the microarray technology of Affymetrix Inc. (Santa Clara, Calif.).

In a first aspect, the present invention provides isolated polynucleotide sequences identified in the attached Sequence Listing as SEQ ID NO: 1-12 and 25, and polypeptide 10 sequences identified in the attached Sequence Listing as SEQ ID NO: 13-24 and 26. The polynucleotides and polypeptides of the present invention have demonstrated similarity to the following antifreeze proteins:

TABLE 1

| SEQ ID NO: DNA | SEQ ID NO: polypeptide | Description |
| --- | --- | --- |
| 1 | 13 | Homologue isolated from *Lolium perenne* of an antifreeze protein that is involved in inhibition of ice crystal growth in plants. In the amino acid sequence, a 7-amino acid repeat (X X N X V X G) was identified (Kuiper et al., Biophys. J. 81: 3560-3565, 2001). The amino acid sequence and conserved domains are shown in FIG. 1. |
| 2 | 14 | Homologue isolated from *Festuca arundinacea* of an antifreeze protein that is involved in inhibition of ice crystal growth in plants. In the amino acid sequence, a 7-amino acid repeat (X X N X V X G) was identified (Kuiper et al., Biophys. J. 81: 3560-3565, 2001). The amino acid sequence and conserved domains are shown in FIG. 2. |
| 3 | 15 | Homologue isolated from *Lolium perenne* of an antifreeze protein that is involved in inhibition of ice crystal growth in plants. In the amino acid sequence, a 7-amino acid repeat (X X N X V X G) was identified (Kuiper et al., Biophys. J. 81: 3560-3565, 2001).The amino acid sequence and conserved domains are shown in FIG. 3. |
| 4 | 16 | Homologue isolated from *Festuca arundinacea* of an antifreeze protein that is involved in inhibition of ice crystal growth in plants. In the amino acid sequence, a 7-amino acid repeat (X X N X V X G) was identified (Kuiper et al., Biophys. J. 81: 3560-3565, 2001). The amino acid sequence and conserved domains are shown in FIG. 4. |
| 5 | 17 | Homolog isolated from *Lolium perenne* of an antifreeze protein that are involved in inhibition of ice crystal growth in plants. In the amino acid sequence, a 7-amino acid repeat (X X N X V X G) was identified (Kuiper et al., Biophys. J. 81: 3560-3565, 2001). The amino acid sequence and conserved domains are shown in FIG. 5 |
| 6 | 18 | Homologue isolated from *Festuca arundinacea* of an antifreeze protein that is involved in inhibition of ice crystal growth in plants. In the amino acid sequence, a 7-amino acid repeat (X X N X V X G) was identified (Kuiper et al., Biophys. J. 81: 3560-3565, 2001). The amino acid sequence and conserved domains are shown in FIG. 6 |

TABLE 1-continued

| SEQ ID NO: DNA | SEQ ID NO: polypeptide | Description |
|---|---|---|
| 7 | 19 | Homologue isolated from *Lolium perenne* of an antifreeze protein that is involved in inhibition of ice crystal growth in plants. In the amino acid sequence, a 7-amino acid repeat (X X N X V X G) was identified (Kuiper et al., Biophys. J. 81: 3560-3565, 2001). The amino acid sequence and conserved domains are shown in FIG. 7 |
| 8 | 20 | Homologue isolated from *Lolium perenne* of an antifreeze protein that is involved in inhibition of ice crystal growth in plants. In the amino acid sequence, a 7-amino acid repeat (X X N X V X G) was identified (Kuiper et al., Biophys. J. 81: 3560-3565, 2001). The amino acid sequence and conserved domains are shown in FIG. 8 |
| 9 | 21 | Homologue isolated from *Festuca arundinacea* of an antifreeze protein that is involved in inhibition of ice crystal growth in plants. In the amino acid sequence, a 7-amino acid repeat (X X N X V X G) was identified (Kuiper et al., Biophys. J. 81: 3560-3565, 2001). The amino acid sequence and conserved domains are shown in FIG. 9. |
| 10 | 22 | Homologue isolated from *Lolium perenne* of an antifreeze protein that is involved in inhibition of ice crystal growth in plants. In the amino acid sequence, a 7-amino acid repeat (X X N X V X G) was identified (Kuiper et al., Biophys. J. 81: 3560-3565, 2001). The amino acid sequence and conserved domains are shown in FIG. 10. |
| 11 | 23 | Homologue isolated from *Festuca arundinacea* of an antifreeze protein that is involved in inhibition of ice crystal growth in plants. In the amino acid sequence, a 7-amino acid repeat (X X N X V X G) was identified (Kuiper et al., Biophys. J. 81: 3560-3565, 2001). The amino acid sequence and conserved domains are shown in FIG. 11. |
| 12 | 24 | Homologue isolated from *Lolium perenne* of an antifreeze protein that is involved in inhibition of ice crystal growth in plants. In the amino acid sequence, a 7-amino acid repeat (X X N X V X G) was identified (Kuiper et al., Biophys. J. 81: 3560-3565, 2001). The amino acid sequence and conserved domains are shown in FIG. 12. |
| 25 | 26 | Homologue isolated from *Lolium perenne* of an antifreeze protein that is involved in inhibition of ice crystal growth in plants. In the amino acid sequence, a 7-amino acid repeat (X X N X V X G) was identified (Kuiper et al., Biophys. J. 81: 3560-3565, 2001). The amino acid sequence and conserved domains are shown in FIG. 13. |

As used herein, the term "antifreeze protein" refers to proteins that possess an ability to inhibit, or alter the growth of ice crystals. As discussed above, these proteins bind to ice crystals thereby inhibiting their growth, and enabling some plants and organisms to survive under freezing conditions (Kuiper et al., *Biophys. J.* 81:3560-3565, 2001). The antifreeze proteins are generally hydrophilic and are high in asparagine, valine, serine, and threonine residues (Sidebottom et al., *Nature* 406:256, 2000).

All the polynucleotides and polypeptides provided herein are isolated and purified, as those terms are commonly used in the art. Preferably, the polypeptides and polynucleotides are at least about 80% pure, more preferably at least about 90% pure, and most preferably at least about 99% pure.

The word "polynucleotide(s)," as used herein, means a polymeric collection of nucleotides, and includes DNA and corresponding RNA molecules and both single and double stranded molecules, including HnRNA and mRNA molecules, sense and anti-sense strands of DNA and RNA molecules, and comprehends cDNA, genomic DNA, and wholly or partially synthesized polynucleotides. A polynucleotide of the present invention may be an entire gene, or any portion thereof. As used herein, a "gene" is a DNA sequence which codes for a functional protein or RNA molecule. Operable anti-sense polynucleotides may comprise a fragment of the corresponding polynucleotide, and the definition of "polynucleotide" therefore includes all operable anti-sense fragments. Anti-sense polynucleotides and techniques involving anti-sense polynucleotides are well known in the art and are described, for example, in Robinson-Benion et al., *Methods in Enzymol.* 254(23): 363-375, 1995 and Kawasaki et al., *Artific. Organs* 20(8): 836-848, 1996.

In specific embodiments, the present invention provides isolated polynucleotides comprising a sequence of SEQ ID NO: 1-12 or 25; polynucleotides comprising variants of SEQ ID NO: 1-12 or 25; polynucleotides comprising extended sequences of SEQ ID NO: 1-12 or 25 and their variants, oligonucleotide primers and probes corresponding to the sequences set out in SEQ ID NO: 1-12 or 25 and their variants, polynucleotides comprising at least a specified number of contiguous residues of any of SEQ ID NO: 1-12 or 25 (x-mers), and polynucleotides comprising extended sequences which include portions of the sequences set out in SEQ ID NO: 1-12 and 25, all of which are referred to herein, collectively, as "polynucleotides of the present invention." Polynucleotides that comprise complements of such polynucleotide sequences, reverse complements of such polynucleotide sequences, or reverse sequences of such polynucleotide sequences, together with variants of such sequences, are also provided.

The definition of the terms "complement(s)," "reverse complement(s)," and "reverse sequence(s)," as used herein, is best illustrated by the following example. For the sequence 5'0 AGGACC 3', the complement, reverse complement, and reverse sequence are as follows:

```
complement          3' TCCTGG 5'
reverse complement  3' GGTCCT 5'
reverse sequence    5' CCAGGA 3'.
```

Preferably, sequences that are complements of a specifically recited polynucleotide sequence are complementary over the entire length of the specific polynucleotide sequence.

As used herein, the term "x-mer," with reference to a specific value of "x," refers to a polynucleotide comprising at least a specified number ("x") of contiguous residues of: any of the polynucleotides provided in SEQ ID NO: 1-12 and 25. The value of x may be from about 20 to about 600, depending upon the specific sequence.

Polynucleotides of the present invention comprehend polynucleotides comprising at least a specified number of contiguous residues (x-mers) of any of the polynucleotides identified as SEQ ID NO: 1-12 and 25, or their variants. Similarly, polypeptides of the present invention comprehend polypeptides comprising at least a specified number of contiguous residues (x-mers) of any of the polypeptides identified as SEQ ID NO: 13-24 and 26. According to preferred embodiments, the value of x is at least 20, more preferably at least 40, more preferably yet at least 60, and most preferably at least 80. Thus, polynucleotides of the present invention include polynucleotides comprising a 20-mer, a 40-mer, a 60-mer, an 80-mer, a 100-mer, a 120-mer, a 150-mer, a 180-mer, a 220-mer, a 250-mer; or a 300-mer, 400-mer, 500-mer or 600-mer of a polynucleotide provided in SEQ ID NO: 1-12 and 25, or a variant of one of the polynucleotides corresponding to the polynucleotides provided in SEQ ID NO: 1-12 and 25. Polypeptides of the present invention include polypeptides comprising a 20-mer, a 40-mer, a 60-mer, an 80-mer, a 100-mer, a 120-mer, a 150-mer, a 180-mer, a 220-mer, a 250-mer; or a 300-mer, 400-mer, 500-mer or 600-mer of a polypeptide provided in SEQ ID NO: 13-24 and 26, or a variant thereof.

Polynucleotides disclosed herein were isolated by high throughput sequencing of cDNA libraries comprising forage grass tissue collected from *Lolium perenne* and *Festuca arundinacea*. Some of the polynucleotides disclosed herein may be "partial" sequences, in that they do not represent a full-length gene encoding a full-length polypeptide. Such partial sequences may be extended by analyzing and sequencing various DNA libraries using primers and/or probes and well known hybridization and/or PCR techniques. Partial sequences may be extended until an open reading frame encoding a polypeptide, a full-length polynucleotide and/or gene capable of expressing a polypeptide, or another useful portion of the genome is identified. Such extended sequences, including full-length polynucleotides and genes, are described as "corresponding to" a sequence identified as one of the sequences of SEQ ID NO: 1-12 and 25 or a variant thereof, or a portion of one of the sequences of SEQ ID NO: 1-12 and 25 or a variant thereof, when the extended polynucleotide comprises an identified sequence or its variant, or an identified contiguous portion (x-mer) of one of the sequences of SEQ ID NO: 1-12 and 25 or a variant thereof. Similarly, RNA sequences, reverse sequences, complementary sequences, anti-sense sequences and the like, corresponding to the polynucleotides of the present invention, may be routinely ascertained and obtained using the cDNA sequences identified as SEQ ID NO: 1-12 and 25.

The polynucleotides identified as SEQ ID NO: 1-12 and 25 contain open reading frames ("ORFs") encoding polypeptides and functional portions of polypeptides. Additionally, open reading frames encoding polypeptides may be identified in extended or full length sequences corresponding to the sequences set out as SEQ ID NO: 1-12 and 25. Open reading frames may be identified using techniques that are well known in the art. These techniques include, for example, analysis for the location of known start and stop codons, most likely reading frame identification based on codon frequencies, etc. Suitable tools and software for ORF analysis are well known in the art and include, for example, GeneWise, available from The Sanger Center, Wellcome Trust Genome Campus, Hinxton, Cambridge, CB10 1SA, United Kingdom; Diogenes, available from Computational Biology Centers, University of Minnesota, Academic Health Center, UMHG Box 43, Minneapolis Minn. 55455; and GRAIL, available from the Informatics Group, Oak Ridge National Laboratories, Oak Ridge, Tennessee Tenn. Once a partial open reading frame is identified, the polynucleotide may be extended in the area of the partial open reading frame using techniques that are well known in the art until the polynucleotide for the full open reading frame is identified.

Once open reading frames are identified in the polynucleotides of the present invention, the open reading frames may be isolated and/or synthesized. Expressible genetic constructs comprising the open reading frames and suitable promoters, initiators, terminators, etc., which are well known in the art, may then be constructed. Such genetic constructs may be introduced into a host cell to express the polypeptide encoded by the open reading frame. Suitable host cells may include various prokaryotic and eukaryotic cells, including plant cells, mammalian cells, archaeal cells, bacterial cells, algae and the like.

The polynucleotides disclosed herein may be isolated by high throughput sequencing of cDNA libraries prepared from forage grass tissue, as described below in Example 1. Alternatively, oligonucleotide probes and primers based on the sequences provided in SEQ ID NO: 1-12 and 25 can be synthesized as detailed below, and used to identify positive clones in either cDNA or genomic DNA libraries from forage grass tissue cells by means of hybridization or polymerase chain reaction (PCR) techniques. Hybridization and PCR techniques suitable for use with such oligonucleotide probes are well known in the art (see, for example, Mullis et al., *Cold Spring Harbor Symp. Quant. Biol.*, 51:263, 1987; Erlich, ed., *PCR technology*, Stockton Press: NY, 1989; and Sambrook et al., eds., *Molecular cloning: a laboratory manual*, 2nd ed., CSHL Press: Cold Spring Harbor, N.Y., 1989). In addition to DNA-DNA hybridization, DNA-RNA or RNA-RNA hybridization assays are also possible. In the first case, the mRNA from expressed genes would then be detected instead of genomic DNA or cDNA derived from mRNA of the sample. In the second case, RNA probes could be used. Artificial analogs of DNA hybridizing specifically to target sequences could also be employed. Positive clones can be analyzed by using restriction enzyme digestion, DNA sequencing or the like.

The polynucleotides disclosed herein may also, or alternatively, be synthesized using techniques that are well known in the art. The polynucleotides may be synthesized, for example, using automated oligonucleotide synthesizers (e.g., Beckman Oligo 1000M DNA Synthesizer; Beckman Coulter Ltd., Fullerton, Calif.) to obtain polynucleotide segments of up to 50 or more nucleic acids. A plurality of such polynucleotide segments may then be ligated using standard DNA manipulation techniques that are well known in the art of molecular biology. One conventional and exemplary polynucleotide synthesis technique involves synthesis of a single stranded polynucleotide segment having, for example, 80 nucleic acids, and hybridizing that segment to a synthesized complementary 85 nucleic acid segment to produce a 5 nucleotide overhang. The next segment may then be synthesized in a similar fashion, with a 5 nucleotide overhang on the opposite strand. The "sticky" ends ensure proper ligation when the two portions are hybridized. In this way, a complete polynucleotide of the present invention may be synthesized entirely in vitro.

Oligonucleotide probes and primers complementary to and/or corresponding to SEQ ID NO: 1-12 and 25 and variants of those sequences, are also comprehended by the present invention. Such oligonucleotide probes and primers are substantially complementary to the polynucleotide of interest over a certain portion of the polynucleotide. An oligonucleotide probe or primer is described as "corresponding to" a polynucleotide disclosed herein, including one of the sequences set out as SEQ ID NO: 1-12 and 25 or a variant thereof, if the oligonucleotide probe or primer, or its complement, is contained within one of the sequences set out as SEQ ID NO: 1-12 and 25 or a variant of one of the specified sequences.

Two single stranded sequences are said to be substantially complementary when the nucleotides of one strand, optimally aligned and compared, with the appropriate nucleotide insertions and/or deletions, pair with at least 80%, preferably at least .90% to 95%, and more preferably at least 98% to 100%, of the nucleotides of the other strand. Alternatively, substantial complementarity exists when a first DNA strand will selectively hybridize to a second DNA strand under stringent hybridization conditions.

In specific embodiments, the oligonucleotide probes and/or primers comprise at least about 6 contiguous residues, more preferably at least about 10 contiguous residues, and most preferably at least about 20 contiguous residues complementary to a polynucleotide sequence of the present invention. Probes and primers of the present invention may be from about 8 to 100 base pairs in length, preferably from about 10 to 50 base pairs in length, and more preferably from about 15 to 40 base pairs in length. The probes can be easily selected using procedures well known in the art, taking into account DNA-DNA hybridization stringencies, annealing and melting temperatures, potential for formation of loops, and other factors that are well known in the art. Preferred techniques for designing PCR primers are disclosed in Dieffenbach and Dyksler, PCR Primer: *a laboratory manual*, CSHL Press: Cold Spring Harbor, N.Y., 1995. A software program suitable for designing probes, and especially for designing PCR primers, is available from Premier Biosoft International, 3786 Corina Way, Palo Alto, Calif. 94303-4504.

The isolated polynucleotides disclosed herein also have utility in genome mapping, in physical mapping, and in positional cloning of genes.

The polynucleotides identified as SEQ ID NO: 1-12 and 25 were isolated from cDNA clones and represent sequences that are expressed in the tissue from which the cDNA was prepared. RNA sequences, reverse sequences, complementary sequences, anti-sense sequences, and the like, corresponding to the polynucleotides disclosed herein, may be routinely ascertained and obtained using the cDNA sequences identified as SEQ ID NO: 1-12 and 25.

Identification of genomic DNA and heterologous species DNA can be accomplished by standard DNA/DNA hybridization techniques, under appropriately stringent conditions, using all or part of a polynucleotide sequence as a probe to screen an appropriate library. Alternatively, PCR techniques using oligonucleotide primers that are designed based on known genomic DNA, cDNA and protein sequences can be used to amplify and identify genomic and cDNA sequences.

In another aspect, isolated polypeptides encoded by the above polynucleotides are provided. As used herein, the term "polypeptide" encompasses amino acid chains of any length, including full-length proteins, wherein the amino acid residues are linked by covalent peptide bonds. The term "polypeptide encoded by a polynucleotide" as used herein, includes polypeptides encoded by a polynucleotide that comprises a partial isolated polynucleotide sequence provided herein. In specific embodiments, the polypeptides disclosed herein comprise an amino acid sequence selected from the group consisting of SEQ ID NO: 13-24 and 26, as well as variants of such sequences.

As noted above, polypeptides disclosed herein may be produced recombinantly by inserting a polynucleotide sequence of the present invention encoding the polypeptide into an expression vector and expressing the polypeptide in an appropriate host. Any of a variety of expression vectors known to those of ordinary skill in the art may be employed. Expression may be achieved in any appropriate host cell that has been transformed or transfected with an expression vector containing a polynucleotide molecule that encodes a recombinant polypeptide. Suitable host cells include prokaryotes, yeast, and higher eukaryotic cells. Preferably, the host cells employed are plant, *Escherichia coli*, insect, yeast, or a mammalian cell line such as COS or CHO. The polynucleotide sequences expressed in this manner may encode naturally occurring polypeptides, portions of naturally occurring polypeptides, or other variants thereof. The expressed polypeptides may be used in various assays known in the art to determine their biological activity. Such polypeptides may also be used to raise antibodies, to isolate corresponding interacting proteins or other compounds, and to quantitatively determine levels of interacting proteins or other compounds.

In a related aspect, polypeptides are provided that comprise at least a functional portion of a polypeptide having an amino acid sequence selected from the group consisting of sequences provided in SEQ ID NO: 13-24 and 26, and variants thereof. As used herein, the "functional portion" of a polypeptide is that portion which contains an active site essential for affecting the function of the polypeptide, for example, that portion of the molecule that is capable of binding ice crystals. The active site may be made up of separate portions present on one or more polypeptide chains and will generally exhibit high binding affinity. Functional portions of a polypeptide may be identified by first preparing fragments of the polypeptide by either chemical or enzymatic digestion of the polypeptide, or by mutation analysis of the polynucleotide that encodes the polypeptide and subsequent expression of the resulting mutant polypeptides. The polypeptide fragments or mutant polypeptides are then tested to determine which portions retain biological activity, using methods well known to those of skill in the art, including the representative assays described below.

Portions and other variants of the inventive polypeptides may be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85: 2149-2146, 1963. Equipment for automated synthesis of polypeptides is commercially available from suppliers such as Perkin Elmer/Applied Biosystems, Inc. (Foster City, Calif.), and may be operated according to the manufacturer's instructions. Variants of a native polypeptide may be prepared using standard mutagenesis techniques, such as oligonucleotide-directed site-specific mutagenesis (Kunkel, *Proc. Natl. Acad. Sci. USA* 82: 488-492, 1985). Sections of DNA sequences may also be removed using standard techniques to permit preparation of truncated polypeptides.

As used herein, the term "variant" comprehends nucleotide or amino acid sequences different from the specifically identified sequences, wherein one or more nucleotides or amino acid residues is deleted, substituted, or added. Variants may be naturally occurring allelic variants, or non-naturally occurring variants. Variant sequences (polynucleotide or polypeptide) preferably exhibit at least 75%, more preferably at least 80%, more preferably at least 90%, more preferably yet at least 95%, and most preferably, at least 98% identity to a sequence of the present invention. The percentage identity is determined by aligning the two sequences to be compared as described below, determining the number of identical residues in the aligned portion, dividing that number by the total number of residues in the inventive (queried) sequence, and multiplying the result by 100.

Polynucleotides and polypeptides having a specified percentage identity to a polynucleotide or polypeptide identified in one of SEQ ID NO: 1-26 thus share a high degree of similarity in their primary structure. In addition to a specified percentage identity to a polynucleotide of the present invention, variant polynucleotides and polypeptides preferably have additional structural and/or functional features in common with a polynucleotide of the present invention. Polynucleotides having a specified degree of identity to, or capable of hybridizing to, a polynucleotide of the present invention preferably additionally have at least one of the following features: (1) they contain an open reading frame, or partial open reading frame, encoding a polypeptide, or a functional portion of a polypeptide, having substantially the same functional properties as the polypeptide, or functional portion thereof, encoded by a polynucleotide in a recited SEQ ID NO.; or (2) they contain identifiable domains in common.

Polynucleotide or polypeptide sequences may be aligned, and percentages of identical nucleotides or amino acids in a specified region may be determined against another polynucleotide or polypeptide, using computer algorithms that are publicly available. The BLASTN and FASTA algorithms, set to the default parameters described in the documentation and distributed with the algorithm, may be used for aligning and identifying the similarity of polynucleotide sequences. The alignment and similarity of polypeptide sequences may be examined using the BLASTP algorithm. BLASTX and FASTX algorithms compare nucleotide query sequences translated in all reading frames against polypeptide sequences. The FASTA and FASTX algorithms are described in Pearson and Lipman, *Proc. Natl. Acad. Sci. USA* 85:2444-2448, 1988; and in Pearson, *Methods in Enzymol.* 183:63-98, 1990. The FASTA software package is available from the University of Virginia by contacting the Assistant Provost for Research, University of Virginia, PO Box 9025, Charlottesville, Va. 22906-9025. The BLASTN software is available from the National Center for Biotechnology Information (NCBI), National Library of Medicine, Building 38A, Room 8N805, Bethesda, Md. 20894. The BLASTN algorithm Version 2.0.11 [Jan. 20, 2000] set to the default parameters described in the documentation and distributed with the algorithm, is preferred for use in the determination of polynucleotide variants according to the present invention. The use of the BLAST family of algorithms, including BLASTN, BLASTP and BLASTX, is described in the publication of Altschul et al., "Gapped BLAST and PSI-BLAST: a new generation of protein database search programs," *Nucleic Acids Res.* 25:3389-3402, 1997.

The following running parameters are preferred for determination of alignments and similarities using BLASTN that contribute to the E values and percentage identity for polynucleotides: Unix running command with the following default parameters: blastall -p blastn -d embldb -e 10 -G 0 -E 0 -FF -r 1 -v 30 -b 30 -i queryseq -o results; and parameters are: -p Program Name [String]; -d Database [String]; -e Expectation value (E) [Real]; -G Cost to open a gap (zero invokes default behavior) [Integer]; -E Cost to extend a gap (zero invokes default behavior) [Integer]; -FF low complexity filter; -r Reward for a nucleotide match (BLASTN only) [Integer]; -v Number of one-line descriptions (V) [Integer]; -b Number of alignments to show (B) [Integer]; -i Query File [File In]; -o BLAST report Output File [File Out] Optional.

The following running parameters are preferred for determination of alignments and similarities using BLASTP that contribute to the E values and percentage identity of polypeptide sequences: blastall -p blastp -d swissprot-trembledb -e 10 -G 0 -E 0 -FF -v 30 -b 30 -i queryseq -o results; the parameters are: -p Program Name [String]; -d Database [String]; -e Expectation value (E) [Real]; -G Cost to open a gap (zero invokes default behavior) [Integer]; -E Cost to extend a gap (zero invokes default behavior) [Integer]; -FF low complexity filter; -v Number of one-line descriptions (v) [Integer]; -b Number of alignments to show (b) [Integer]; -I Query File [File In]; -o BLAST report Output File [File Out] Optional.

The "hits" to one or more database sequences by a queried sequence produced by BLASTN, BLASTP, FASTA, or a similar algorithm, align and identify similar portions of sequences. The hits are arranged in order of the degree of similarity and the length of sequence overlap. Hits to a database sequence generally represent an overlap over only a fraction of the sequence length of the queried sequence.

As noted above, the percentage identity of a polynucleotide or polypeptide sequence is determined by aligning polynucleotide and polypeptide sequences using appropriate algorithms, such as BLASTN or BLASTP, respectively, set to default parameters; identifying the number of identical nucleic or amino acids over the aligned portions; dividing the number of identical nucleic or amino acids by the total number of nucleic or amino acids of the polynucleotide or polypeptide of the present invention; and then multiplying by 100 to determine the percentage identity. By way of example, a queried polynucleotide having 220 nucleic acids has a hit to a polynucleotide sequence in the EMBL database having 520 nucleic acids over a stretch of 23 nucleotides in the alignment produced by the BLASTN algorithm using the default parameters. The 23-nucleotide hit includes 21 identical nucleotides, one gap and one different nucleotide. The percentage identity of the queried polynucleotide to the hit in the EMBL database is thus $21/220$ times 100, or 9.5%. The percentage identity of polypeptide sequences may be determined in a similar fashion.

The BLASTN and BLASTX algorithms also produce "Expect" values for polynucleotide and polypeptide alignments. The Expect value (E) indicates the number of hits one can "expect" to see over a certain number of contiguous sequences by chance when searching a database of a certain size. The Expect value is used as a significance threshold for determining whether the hit to a database indicates true similarity. For example, an E value of 0.1 assigned to a polynucleotide hit is interpreted as meaning that in a database of the size of the EMBL database, one might expect to see 0.1 matches over the aligned portion of the sequence with a similar score simply by chance. By this criterion, the aligned and matched portions of the sequences then have a probability of 90% of being related. For sequences having an E value of 0.01 or less over aligned and matched portions, the probability of finding a match by chance in the EMBL database is 1% or less using the BLASTN algorithm. E values for polypeptide sequences may be determined in a similar fashion using various polypeptide databases, such as the SwissProt database.

According to one embodiment, "variant" polynucleotides and polypeptides, with reference to each of the polynucleotides and polypeptides of the present invention, preferably comprise sequences having the same number or fewer nucleotides or amino acids than each of the polynucleotides or polypeptides of the present invention and producing an E value of 0.01 or less when compared to the polynucleotide or polypeptide of the present invention. That is, a variant polynucleotide or polypeptide is any sequence that has at least a 99% probability of being related to the polynucleotide or polypeptide of the present invention, measured as having an E value of 0.01 or less using the BLASTN or BLASTX algorithms set at the default parameters. According to a preferred embodiment, a variant polynucleotide is a sequence having the same number or fewer nucleic acids than a polynucleotide of the present invention that has at least a 99% probability of being related to the polynucleotide of the present invention, measured as having an E value of 0.01 or less using the BLASTN algorithm set at the default parameters. Similarly, according to a preferred embodiment, a variant polypeptide is a sequence having the same number or fewer amino acids than a polypeptide of the present invention that has at least a 99% probability of being related as the polypeptide of the present invention, measured as having an E value of 0.01 or less using the BLASTP algorithm set at the default parameters.

In an alternative embodiment, variant polynucleotides are sequences that hybridize to a polynucleotide of the present invention under stringent conditions. Stringent hybridization conditions for determining complementarity include salt conditions of less than about 1 M, more usually less than about 500 mM, and preferably less than about 200 mM. Hybridization temperatures can be as low as 5° C., but are generally greater than about 22° C., more preferably greater than about 30° C., and most preferably greater than about 37° C. Longer DNA fragments may require higher hybridization temperatures for specific hybridization. Since the stringency of hybridization may be affected by other factors such as probe composition, presence of organic solvents, and extent of base mismatching, the combination of parameters is more important than the absolute measure of any one alone. An example of "stringent conditions" is prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

The present invention also encompasses polynucleotides that differ from the disclosed sequences but that, as a consequence of the discrepancy of the genetic code, encode a polypeptide having similar functional activity to a polypeptide encoded by a polynucleotide of the present invention. Thus, polynucleotides comprising sequences that differ from the polynucleotide sequences recited in SEQ ID NO: 1-12 and 25, or complements, reverse sequences, or reverse complements of those sequences, as a result of conservative substitutions are contemplated by and encompassed within the present invention. Additionally, polynucleotides comprising sequences that differ from the polynucleotide sequences recited in SEQ ID NO: 1-12 and 25, or complements, reverse complements or reverse sequences thereof, as a result of deletions and/or insertions totaling less than 10% of the total sequence length are also contemplated by and encompassed within the present invention. Similarly, polypeptides comprising sequences that differ from the polypeptide sequences recited in SEQ ID NO: 13-24 and 26 as a result of amino acid substitutions, insertions, and/or deletions totaling less than 10% of the total sequence length are contemplated by and encompassed within the present invention, provided the variant polypeptide has activity in a lignin, fructan or tannin biosynthetic pathway.

In another aspect, the present invention provides genetic constructs comprising, in the 5'-3' direction, a gene promoter sequence; an open reading frame coding for at least a functional portion of a polypeptide of the present invention; and a gene termination sequence. The open reading frame may be orientated in either a sense or anti-sense direction. For applications where amplification of cold tolerance is desired, the open reading frame may be inserted in the construct in a sense orientation, such that transformation of a target organism with the construct will lead to an increase in the number of copies of the gene and therefore an increase in the amount of polypeptide. When down-regulation of cold tolerance is desired, the open reading frame may be inserted in the construct in an anti-sense orientation, such that the RNA produced by transcription of the polynucleotide is complementary to the endogenous mRNA sequence. This, in turn, will result in a decrease in the number of copies of the gene and therefore a decrease in the amount of polypeptide. Alternatively, regulation may be achieved by inserting appropriate sequences or subsequences (e.g., DNA or RNA) in ribozyme constructs.

Genetic constructs comprising a non-coding region of a gene coding for a polypeptide of the present invention, or a nucleotide sequence complementary to a non-coding region, together with a gene promoter sequence and a gene termination sequence, are also provided. As used herein the term "non-coding region" includes both transcribed sequences that are not translated, and non-transcribed sequences within about 2000 base pairs 5' or 3' of the translated sequences or open reading frames. Examples of non-coding regions that may be usefully employed in the inventive constructs include introns and 5'-non-coding leader sequences. Transformation of a target organism with such a genetic construct may lead to a reduction in the cold tolerance the plant by the process of cosuppression, in a manner similar to that discussed, for example, by Napoli et al., *Plant Cell* 2:279-290, 1990; and de Carvalho Niebel et al., *Plant Cell* 7:347-358, 1995.

The genetic constructs of the present invention further comprise a gene promoter sequence and a gene termination sequence, operably linked to the polynucleotide to be transcribed, which control expression of the gene. The gene promoter sequence is generally positioned at the 5' end of the polynucleotide to be transcribed, and is employed to initiate transcription of the polynucleotide. Gene promoter sequences are generally found in the 5' non-coding region of a gene but they may exist in introns (Luehrsen, *Mol. Gen. Genet.* 225:81-93, 1991). When the construct includes an open reading frame in a sense orientation, the gene promoter sequence also initiates translation of the open reading frame.

For genetic constructs comprising either an open reading frame in an anti-sense orientation or a non-coding region, the gene promoter sequence consists only of a transcription initiation site having a RNA polymerase binding site.

A variety of gene promoter sequences that may be usefully employed in the genetic constructs of the present invention are well known in the art. The promoter gene sequence, and also the gene termination sequence, may be endogenous to the target host or may be exogenous, provided the promoter is functional in the target host. For example, the promoter and termination sequences may be from other plant species, plant viruses, bacterial or archaeal plasmids and the like. Preferably, gene promoter and termination sequences are from the inventive sequences themselves.

Factors influencing the choice of promoter include the desired tissue specificity of the construct, and the timing of transcription and translation. For example, constitutive promoters, such as the 35S Cauliflower Mosaic Virus (CaMV 35S) promoter, will affect the activity of the enzyme in all parts of the plant. Use of a tissue specific promoter will result in production of the desired sense or anti-sense RNA only in the tissue of interest. With genetic constructs employing inducible gene promoter sequences, the rate of RNA polymerase binding and initiation can be modulated by external physical or chemical stimuli, such as light, heat, anaerobic stress, alteration in nutrient conditions and the like. Temporally regulated promoters can be employed to effect modulation of the rate of RNA polymerase binding and initiation at a specific time during development of a transformed cell. Preferably, the original promoters from the gene in question, or promoters from a specific tissue-targeted gene in the organism to be transformed, such as *Lolium* or *Festuca*, are used. Promoters different from the original gene may also be usefully employed in the inventive genetic constructs in order to prevent feedback inhibition. Other examples of gene promoters which may be usefully employed in the present invention include, mannopine synthase (mas), octopine synthase (ocs) and those reviewed by Chua et al., *Science* 244:174-181, 1989.

The gene termination sequence, which is located 3' to the polynucleotide to be transcribed, may come from the same gene as the gene promoter sequence or may be from a different gene. Many gene termination sequences known in the art may be usefully employed in the present invention, such as the 3' end of the *Agrobacterium tumefaciens* nopaline synthase gene. However, preferred gene terminator sequences are those from the original gene or from the target species to be transformed.

The genetic constructs of the present invention may also contain a selection marker that is effective in cells, such as plant cells, to allow for the detection of transformed cells containing the inventive construct. Such markers, which are well known in the art, typically confer resistance to one or more toxins. One example of such a marker is the NPTII gene whose expression results in resistance to kanamycin or hygromycin, antibiotics which are usually toxic to plant cells at a moderate concentration (Rogers et al., in Weissbach A and H, eds., *Methods for Plant Molecular Biology*, Academic Press Inc.: San Diego, Calif., 1988). Alternatively, the presence of the desired construct in transformed cells can be determined by means of other techniques well known in the art, such as Southern and Western blots.

Techniques for operatively linking the components of the inventive genetic constructs are well known in the art and include the use of synthetic linkers containing one or more restriction endonuclease sites as described, for example, by Sambrook et al., (*Molecular cloning: a laboratory manual*, CSHL Press: Cold Spring Harbor, N.Y., 1989). The genetic construct of the present invention may be linked to a vector having at least one replication system, for example, *Escherichia coli*, whereby after each manipulation, the resulting construct can be cloned and sequenced and the correctness of the manipulation determined.

The genetic constructs of the present invention may be used to transform a variety of organisms including mammals, insects, fungi, archaea and bacteria, in addition to plants, both monocotyledonous (e.g., grasses, maize/corn, grains, oats, rice, sorghum, millet, rye, sugar cane, wheat and barley), dicotyledonous (e.g., *Arabidopsis*, tobacco, legumes, alfalfa, oaks, eucalyptus, maple), and gymnosperms. In a preferred embodiment, the inventive genetic constructs are employed to transform grasses. Preferably the target plant is selected from the group consisting of *Lolium* and *Festuca* species, most preferably from the group consisting of *Lolium perenne* and *Festuca arundinacea*. Other species of ryegrass and fescue that may be usefully transformed with the inventive genetic constructs, include, but are not limited to *Lolium multiflorum* (Italian ryegrass), *Lolium hybridum* (hybrid ryegrass), *Lolium rigidum* (Wimerra grass), *Lolium temulentum* (darnel), *Festuca rubra* (red fescue) and *Festuca pratensis* (meadow fescue). Other plants that may be usefully transformed with the inventive genetic constructs include cold intolerant trees, such as eucalyptus, and high value crops, such as cherries, stone fruit (for example, peaches), apples, pears, walnuts, almonds, peanuts, wine grapes, potatoes and tomatoes. As discussed above, transformation of a organism with a genetic construct of the present invention will produce a modified cold tolerance in the plant.

The production of RNA in target cells may be controlled by choice of the promoter sequence,: or by selecting the number of functional copies or the site of integration of the polynucleotides incorporated into the genome of the target organism. A target organism may be transformed with more than one construct disclosed herein, thereby affecting AFP activity in more than one tissue or affecting AFP activity at more than one expression time. Similarly, a construct may be assembled containing more than one open reading frame coding for an AFP encoded by a polynucleotide disclosed herein or more than one non-coding region of a gene coding for such an AFP. A cooperative effect has been observed in AFPs from winter rye (Wai-Ching Hon et al., *Plant Physiol.* 104:971-980, 1994) and from fish (Mulvihill et al., *J. Biol. Chem.* 255:659-662, 1979; Osuga et al., *J. Biol. Chem.* 235:6669-6672, 1978), indicating that the use of more than AFP may be beneficial. The polynucleotides disclosed herein may also be employed in combination with other known sequences.

Techniques for stably incorporating genetic constructs into the genome of target organisms are well known in the art. Techniques for transforming plants include *Agrobacterium tumefaciens* mediated introduction, electroporation, protoplast fusion, injection into reproductive organs, injection into immature embryos, high velocity projectile introduction and the like. The choice of technique will depend upon the target plant to be transformed. For example, dicotyledonous plants and certain monocots and gymnosperms may be transformed by *Agrobacterium* Ti plasmid technology, as described, for example by Bevan, *Nucleic Acid Res.* 12:8711-8721, 1984. Targets for the introduction of the DNA constructs of the present invention include tissues, such as leaf tissue, disseminated cells, protoplasts, seeds, embryos, meristematic regions; cotyledons, hypocotyls, and the like. Transformation techniques which may be usefully employed in the inventive methods include those taught by Ellis et al., *Plant Cell Reports*, 8:16-20, 1989, Wilson et al., *Plant Cell Reports*

7:704-707, 1989, Tautorus et al., *Theor. Appl. Genet.* 78:531-536, 1989 and Ishida et al., *Nat. Biotechnol.* 14:745-750, 1996.

Once the cells are transformed, cells having the inventive genetic construct incorporated in their genome may be selected by means of a marker, such as the kanamycin resistance marker discussed above. Transgenic cells may then be cultured in an appropriate medium to regenerate whole organisms, such as plants, using techniques well known in the art. In the case of protoplasts, the cell wall is allowed to reform under appropriate osmotic conditions. In the case of seeds or embryos, an appropriate germination or callus initiation medium is employed. For explants, an appropriate regeneration medium is used. Regeneration of plants is well established for many species. The resulting transformed plants may be reproduced sexually or asexually, using methods well known in the art, to give successive generations of transgenic plants.

Polypeptides disclosed herein may be transiently expressed in target plants by means of viral vectors as described, for example by Fischer et al., *Biotechnol. Appl. Biochem.* 30:113-116, 1999. In such methods, a polynucleotide encoding the polypeptide of interest is cloned into the genome of a viral plant pathogen. The resulting infectious recombinant viral transcripts are used to infect plants and produce the polypeptide of interest. Techniques for employing recombinant plant viral vectors to transiently express proteins in plants are will known in the art and include those disclosed in U.S. Pat. No. 6,369,296, the disclosure of which is hereby incorporated by reference. Introduction of the inventive AFPs using such viral vectors is particularly useful for frost protection of fruit trees, where transient expression of AFPs in frost sensitive parts of the trees, such as young floral/fruiting and leaf buds would be very valuable.

Polynucleotides disclosed herein may also be used to specifically suppress gene expression by methods that operate post-transcriptionally to block the synthesis of products of targeted genes, such as RNA interference (RNAi), and quelling. For a review of techniques of gene suppression see *Science*, 288:1370-1372, 2000. Exemplary gene silencing methods are also provided in WO 99/49029 and WO 99/53050. Posttranscriptional gene silencing is brought about by a sequence-specific RNA degradation process which results in the rapid degradation of transcripts of sequence-related genes. Studies have provided evidence that double-stranded RNA may act as a mediator of sequence-specific gene silencing (see, e.g., review by Montgomery and Fire, *Trends in Genetics,* 14: 255-258, 1998). Gene constructs that produce transcripts with self-complementary regions are particularly efficient at gene silencing. A unique feature of this posttranscriptional gene silencing pathway is that silencing is not limited to the cells where it is initiated. The gene-silencing effects may be disseminated to other parts of an organism and even transmitted through the germ line to several generations.

The polynucleotides disclosed herein may be employed to generate gene silencing constructs and or gene-specific self-complementary RNA sequences that can be delivered by conventional art-known methods to tissues, such as plant tissues. Within genetic constructs, sense and antisense sequences can be placed in regions flanking an intron sequence in proper splicing orientation with donor and acceptor splicing sites, such that intron sequences are removed during processing of the transcript and sense and antisense sequences, as well as splice junction sequences, bind together to form double-stranded RNA. Alternatively, spacer sequences of various lengths may be employed to separate self-complementary regions of sequence in the construct. During processing of the gene construct transcript, intron sequences are spliced-out, allowing sense and anti-sense sequences, as well as splice junction sequences, to bind forming double-stranded RNA. Select ribonucleases bind to and cleave the double-stranded RNA, thereby initiating the cascade of events leading to degradation of specific mRNA gene sequences, and silencing specific genes. Alternatively, rather than using a gene construct to express the self-complementary RNA sequences, the gene-specific double-stranded RNA segments are delivered to one or more targeted areas to be internalized into the cell cytoplasm to exert a gene silencing effect. Gene silencing RNA sequences comprising the polynucleotides of the present invention are useful for creating genetically modified plants with desired phenotypes as well as for characterizing genes (e.g., in high-throughput screening of sequences), and studying their functions in intact organisms.

In another embodiment, one or more of the inventive polypeptides may be employed in foliar applicants to protect target plants from damage due to low temperatures and, in particular, from frost and/or freezing. Techniques for preparing and applying foliar applicants are well known and include those described in U.S. Pat. Nos. 6,180,562 and 6,588,142. Preferably, foliar applicants comprising the inventive polypeptides are applied before early spring and early fall/autumn frosts in order to minimize damage to cold intolerant crops.

For use as foliar applicants, the inventive polypeptides may be formulated with known agricultural carriers, such as, but not limited to: water; alcohols; ketones; ethers; aliphatic hydrocarbons; aromatic hydrocarbons; sulfur-containing compounds; and powders of plant or animal origin, such as starch, activated carbon, calcium carbonate, talc, soybean flour, wheat flour. Such formulations may also, or alternatively, contain an adjuvant, such as an extender, penetrant or surfactant. Extenders are adjuvants that can extend the useful life of a spray chemical, by increasing the chemical's adhesion to the leaf, by reducing any factor that can diminish chemical effectiveness, or by enhancing chemical weatherability. Some extenders have the ability to intercept ultraviolet light. Penetrants are adjuvants that help chemicals penetrate plants. Surfactants are adjuvants that reduce the surface tensions of solutions, helping them spread and cover surfaces more effectively. Surfactants are probably the best-known class of adjuvants. Most adjuvants are a double-ended molecule, with one end being water soluble and one end being oil soluble. These molecules can therefore line-up between water-like compounds and oil-like compounds and make them more compatible. Surfactants can be uncharged (non-ionic), positively charged (cationic), or negatively charged (anionic). Specific examples of these compounds include Agral™, Ethokem™, Silwet-77™, Sylgard 309™, Actipron™, Codacide™, Actirob™ and the Brij™ series of compounds.

The resulting formulations may be in any form known in the art, such as liquids, dusts, granules, powders, emulsifiable concentrations, aerosols or pastes, and may be applied by conventional methods, such as spraying, jetting, misting, atomizing, soil application and surface application. The foliar applicants may also include additional components such as emulsifiers, suspending agents, dispersants, wetting agents, thickeners and/or stabilizers, and may be used in combination with other active compounds, such as insecticides, herbicides and fungicides. The amount of polypeptide present within the foliar applicant will vary depending upon the formulation, manner and timing of application, condition of plants, and risk of frost or freeze damage. Preferably the polypeptide is present in a concentration of between 0.1 and 500,000 ppm, preferably between 1 and 100,000 ppm.

In another aspect, methods are provided for using one or more of the inventive polypeptides or polynucleotides to treat disorders in a patient, preferably a mammal, more preferably a human. Disorders that may be treated using the inventive polypeptides and/or polynucleotides include those characterized by the unwanted presence of biocrystals, such as gout and kidney stones.

In this aspect, the polypeptide or polynucleotide is generally present within a composition, such as a pharmaceutical or immunogenic composition. Pharmaceutical compositions may comprise one or more polypeptides, each of which may contain one or more of the above sequences (or variants thereof), and a physiologically acceptable carrier. Immunogenic compositions may comprise one or more of the above polypeptides and an immunostimulant, such as an adjuvant or a liposome, into which the polypeptide is incorporated.

Alternatively, a composition of the present invention may contain DNA encoding one or more polypeptides described herein, such that the polypeptide is generated in situ. In such compositions, the DNA may be present within any of a variety of delivery systems known to those of ordinary skill in the art, including nucleic acid expression systems, and bacterial and viral expression systems. Appropriate nucleic acid expression systems contain the necessary DNA sequences for expression in the patient (such as a suitable promoter and terminator signal). Bacterial delivery systems involve the administration of a bacterium (such as Bacillus Calmette-Guerin) that expresses an immunogenic portion of the polypeptide on its cell surface. In a preferred embodiment, the DNA may be introduced using a viral expression system (e.g., vaccinia or other poxvirus, retrovirus, or adenovirus), which may involve the use of a non-pathogenic, or defective, replication competent virus. Techniques for incorporating DNA into such expression systems are well known in the art. The DNA may also be "naked," as described, for example, in Ulmer et al., Science 259:1745-1749, 1993 and reviewed by Cohen, Science 259:1691-1692, 1993. The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a lipid, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109.

Any of a variety of adjuvants may be employed in the immunogenic compositions of the present invention to non-specifically enhance an immune response. Most adjuvants contain a substance designed to protect the antigen from rapid catabolism, such as aluminum hydroxide or mineral oil, and a non-specific stimulator of immune responses, such as lipid A, Bordetella pertussis or M. tuberculosis. Suitable adjuvants are commercially available as, for example, Freund's Incomplete Adjuvant and Freund's Complete Adjuvant (Difco Laboratories, Detroit, Mich.), and Merck Adjuvant 65 (Merck and Company, Inc., Rahway, N.J.). Other suitable adjuvants include alum, biodegradable microspheres, monophosphoryl lipid A and Quil A.

Routes and frequency of administration of the inventive compositions, as well as dosage, vary from individual to individual. In general, the inventive compositions may be administered by injection (e.g., intradermal, intramuscular, intravenous or subcutaneous), intranasally (e.g., by aspiration) or orally. Preferably, the AFPs of the present invention are injected into the affected area or administered in a topical application which is absorbed by the skin. In general, the amount of polypeptide present in a dose (or produced in situ by the DNA in a dose) ranges from about 1 pg to about 100 mg per kg of host, typically from about 10 pg to about 1 mg per kg of host, and preferably from about 100 pg to about 1 µg per kg of host. Suitable dose sizes will vary with the size of the patient, but will typically range from about 0.1 ml to about 2 ml.

Solutions comprising the inventive polypeptides may also be employed to improve the effectiveness of cryosurgery in, for example, the removal of unwanted tissue, such as tumor tissue. In such methods, the unwanted tissue is perfused with a solution preferably comprising between 1 mg/ml to about 30 mg/ml of the polypeptide. This can be accomplished, for example, by injection into the tissue, ingestion, or perfusion through the vasculature. Once the tissue is perfused with the polypeptide, cryoablation of the tissue is performed using standard techniques employing, for example, a cryogenic probe. Cryogenic probes are preferably used in combination with real-time imaging techniques, such as ultrasound and magnetic resonance imaging.

The inventive polypeptides and/or polynucleotides may also be employed as hydrate inhibitors in, for example, natural gas transmission lines. Gas hydrates form when water molecules crystallize around natural gas guest molecules. This co-crystallization process, which has been recognized for several years, is well characterized and occurs with the right combination of temperature and pressure. Gas hydrates may form in any place where water coexists with natural gas at temperatures as high as 80° F. Long gas transmission lines are particularly vulnerable to hydrate blockage during extended cold weather periods. Sub-sea pipelines may have hydrate problems continually due to the cooling effect of seawater at depth. While there are a few known methods of preventing hydrate formation, thermodynamic solutions such as removing the water, heating the system and lowering the pressure, are often not practical. Another thermodynamic method, the addition of sufficient amounts of ethylene glycol or methanol to decrease hydrate stability, effectively lowers the temperature of hydrate formation. This method requires relatively large amounts of ethylene glycol or methanol, which are inconvenient to use and hazardous due to both chemical toxicity and flammability. This method of treatment can also be quite expensive. Use of the inventive AFPs would be a safer alternative to the use of ethylene glycol and/or methanol Another application of the inventive AFPs is in any spraying process which uses a solution (containing water) at freezing temperatures. One or more of the inventive AFPs could be employed as an anti-clogging agent, by reducing the size of ice crystal to provide a reduced frequency of blocking in the spraying nozzles. This effect might also be applied in the sugar industry where a solution of sugar is sprayed to crystallize and dry it. AFPs could be employed to prevent clogging of the nozzles by reducing and controlling crystal size, with at the same time having the added benefit of reducing drying time.

The following examples are offered by way of illustration and not by way of limitation.

EXAMPLE 1

Isolation of cDNA Sequences from *L. Perenne* and *F. Arundinacea* cDNA Libraries

*L. perenne* and *F. Arundinacea* cDNA expression libraries were constructed and screened as follows. Tissue was collected from *L. perenne* and *F. Arundinacea* during winter and spring, and snap-frozen in liquid nitrogen. The tissues collected include those obtained from leaf blades, leaf base, pseudostem, roots and stem. Total RNA was isolated from each tissue type using TRIzol Reagent (BRL Life Technologies, Gaithersburg, Md.). mRNA from each tissue type was obtained using a Poly(A) Quik mRNA isolation kit (Stratagene, La Jolla, Calif.), according to the manufacturer's specifications. cDNA expression libraries were constructed from the purified mRNA by reverse transcriptase synthesis followed by insertion of the resulting cDNA in Lambda ZAP using a ZAP Express cDNA Synthesis Kit (Stratagene), according to the manufacturer's protocol. The resulting cDNA clones were packaged using a Gigapack II Packaging Extract (Stratagene) employing 1 µl of sample DNA from the 5 µl ligation mix. Mass excision of the libraries was done using XL1-Blue MRF' cells and XLOLR cells (Stratagene) with ExAssist helper phage (Stratagene). The excised phagemids were diluted with NZY broth (Gibco BRL, Gaithersburg, Md.) and plated out onto LB-kanamycin agar plates containing 5-bromo-4-chloro-3-indolyl-beta-D-galactosidase (X-gal) and isopropylthio-beta-galactoside (IPTG).

Of the colonies plated and picked for DNA preparations, the large majority contained an insert suitable for sequencing. Positive colonies were cultured in NZY broth with kanamycin and DNA was purified following standard protocols. Agarose gel at 1% was used to screen sequencing templates for chromosomal contamination. Dye terminator sequences were prepared using a Biomek 2000 robot (Beckman Coulter Inc., Fullerton, Calif.) for liquid handling and DNA amplification using a 9700 PCR machine (Perkin Elmer/Applied Biosystems, Foster City, Calif.) according to the manufacturer's protocol.

The DNA sequences for positive clones were obtained using a Perkin Elmer/Applied Biosystems Division Prism 377 sequencer. cDNA clones were sequenced from the 5' end. The polynucleotide sequences identified as SEQ ID NO: 3 and 10 were identified from *L. perenne* leaf blade cDNA expression libraries; the polynucleotide sequences identified as SEQ ID NO: 8 and 12 were identified from *L. perenne* leaf and pseudostem cDNA expression libraries; the polynucleotide sequence identified as SEQ ID NO: 1 was identified from *L. perenne* pseudostem cDNA expression libraries; the polynucleotide sequences identified as SEQ ID NO: 5, 6 and 25 were identified from a *L. perenne* root cDNA expression library; the polynucleotide sequences identified as SEQ ID NO: 4, 7, 9 and 11 were identified from *F. Arundinacea* leaf blade cDNA expression libraries; and the polynucleotide sequence identified as SEQ ID NO: 2 was identified from *F. Arundinacea* basal stem cDNA expression libraries. All of the sequences of SEQ ID NO: 1-12 are believed to be full-length. The amino acid sequences corresponding to the cDNA sequences of SEQ ID NO: 1-12 and 25 are provided in SEQ ID NO: 13-24 and 26, respectively.

BLASTN Polynucleotide Analysis

The isolated cDNA sequences were compared to sequences in the EMBL DNA database using the computer algorithm BLASTN. Comparisons of DNA sequences provided in SEQ ID NO: 1-12 to sequences in the EMBL DNA database were made as of Aug. 23, 2002, using BLASTN algorithm Version 2.0.11 [Jan. 20, 2000] and the following Unix running command: blastall -p blastn -d embldb -e 10 -G0 -E0 -FF -r 1 -v 30 -b 30 -i queryseq -o. Comparisons of the DNA sequence provided in SEQ ID NO: 25 to sequences in the EMBL DNA database were made as of Aug. 15, 2003, using BLASTN algorithm Version 2.0.11 [Jan. 20, 2000] and the same Unix running command.

The sequences of SEQ ID NO: 1-12 and 25 were determined to have less than 50% identity to sequences in the EMBL database using the computer algorithm BLASTN, as described above.

BLASTP Polypeptide Analysis

Comparisons of protein sequences provided in SEQ ID NOS: 13-24, to sequences in the SwissProt-TrEMBLE protein database were made as of Aug. 23, 2002 using BLASTP algorithm Version 2.0.11 [Jan. 20, 2000], and the following Unix running command: blastall -p blastp -d swissprottrembledb -e 10 -G0 -E0 -FF -v 30 -b 30 -i queryseq -o. Comparison of the protein sequence provided in SEQ ID NO: 26 to sequences in the SwissProt-TrEMBLE protein database were made as of Aug. 15, 2003 using BLASTP algorithm Version 2.0.11 [Jan. 20, 2000] and the same Unix running command.

The sequences of SEQ ID NO: 13-24 and 26 were determined to have less than 50% identity to sequences in the SwissProt-TrEMBLE database determined as described above using the computer algorithm BLASTP.

BLASTX Polynucleotide Analysis

Comparisons of DNA sequences provided in SEQ ID NO: 1-12, to sequences in the SwissProt-TrEMBLE protein database (using BLASTX) were made as of Aug. 23, 2002 using BLAST algorithm Version 2.0.11 [Jan. 20, 2000], and the following Unix running command: blastall -p blastx -d swissprottrembledb -e 10 -G0 -E0 -FF -v 30 -b 30 -i queryseq -o. Comparison of the DNA sequence provided in SEQ ID NO: 25 to sequences in the SwissProt-TrEMBLE protein database (using BLASTX) were made as of Aug. 15, 2003 using algorithm Version 2.0.11 [Jan. 20, 2000] and the same Unix running command.

The sequences of SEQ ID NO: 1-12 and 25 were determined to have less than 50% identity to sequences in the SwissProt-TrEMBLE database, determined as described above using the computer algorithm BLASTX.

The location of open reading frames (ORFs), by nucleotide position, contained within the sequences of SEQ ID NO: 1-12 and 25, and the corresponding amino acid sequences are provided in Table 2 below.

TABLE 2

| POLYNUCLEOTIDE SEQ ID NO: | ORF | POLYPEPTIDE SEQ ID NO: |
|---|---|---|
| 1 | 55-786 | 13 |
| 2 | 82-813 | 14 |
| 3 | 35-838 | 15 |
| 4 | 41-850 | 16 |
| 5 | 60-905 | 17 |
| 6 | 77-910 | 18 |
| 7 | 59-892 | 19 |
| 8 | 55-897 | 20 |
| 9 | 53-910 | 21 |
| 10 | 79-843 | 22 |
| 11 | 53-841 | 23 |
| 12 | 72-842 | 24 |
| 25 | 59-904 | 26 |

EXAMPLE 2

Use of Grass Anti-Freeze Protein Genes to Alter Ice Crystal Structure

Transformation of *Arabidopsis* plants with grass Anti-Freeze Protein Genes

Sense constructs containing a polynucleotide including the coding region of AFP genes isolated from *Lolium perenne* or *Festuca arundinacea* (SEQ ID NOS: 1, 3, 5, 8 and 10) were inserted into a binary vector and used to transform *Agrobacterium tumefaciens* LBA4404 using published methods (see, An G, Ebert P R, Mitra A, Ha S B, "Binary Vectors," in Gelvin S B, Schilperoort R A, eds., *Plant Molecular Biology Manual*, Kluwer Academic Publishers: Dordrecht, 1988). The presence and integrity of the binary vector in *A. tumefaciens* was verified by the polymerase chain reaction (PCR) using vector primers.

The *A. tumefaciens* containing the sense gene constructs were used to transform *Arabidopsis*, by floral dipping (Clough and Bent, *Plant J.* 16:735-743, 1998). Several independent transformed plant lines were established for the sense construct for each gene. Transformed plants were allowed to self fertilize and T1 seed collected. A number of T2 plants from each original T1 plant were tested to confirm the presence of the appropriate anti-freeze gene construct by PCR analysis of genomic DNA. The primers listed in SEQ ID NOS: 27 and 28 were used for AFP1 (SEQ ID NO: 1), the primers listed in SEQ ID NOS: 29 and 30 were used for AFP2 (SEQ ID NO: 3), the primers listed in SEQ ID NOS: 31 and 32 were used for AFP4 (SEQ ID NO: 8), and the primers listed in SEQ ID NOS: 33 and 34 were used for AFP5L (SEQ ID NO: 10). No transgene was seen in the empty-vector transformed control plants.

Increased Freezing Tolerance of the AFP-expressing Plants

Plants are tested for increased survival after enduring freezing conditions, in comparison to wild type empty vector control *Arabidopsis*. A plate-based assay is employed, similar to previous assays that tested *Arabidopsis* mutants for changes in freezing tolerance (Chinnusamy et al., *Genes Dev.* 17:1043-1054, 2003). Briefly, 90 T2 seedlings of each line, 10 independent transgenic lines per construct, are sown on to MS plus sucrose agar plates. The seed is stratified at 4° C. for 2 days before germinating at 22° C. for 10 days, followed by a 4 day cold acclimation at 4° C., low light. The seedlings are then subjected to a freezing cycle in a controlled environment unit. Plates are incubated at −1° C. for 16 hours and sprinkled with ice chips to attain even freezing. The temperature is lowered at 1° C. per hour to either—10° C. or −12° C. and the minimum temperature is maintained for 2 hours before placing the plants at 4° C. for 12 hours to thaw. The plants are then kept at 22° C. and visually scored for survival after 2 days.

EXAMPLE 3

Use of Grass Anti-Freeze Protein Genes to Change Ice Crystal Size in Sucrose Solutions A number of grass anti-freeze protein genes (SEQ ID NO: 1, 3, 5, and 11), as well as a truncated gene derived from AFP1 (SEQ ID NO: 1), were expressed in *Escherichia coli* and purified using standard protocols. The grass genes were amplified by PCR using the forward and reverse primers listed in SEQ ID NO: 35 and 36 for AFP1 (SEQ ID NO: 1), SEQ ID NO: 39 and 40 for AFP2 (SEQ ID NO: 3), SEQ ID NO: 41 and 42 for AFP3 (SEQ ID NO: 5), and SEQ ID NO: 43 and 44 for AFP5 (SEQ ID NO: 11). The truncated AFP1 gene was amplified using the primers given in SEQ ID NO: 37 and 38. The resulting fragments were cloned into a modified pET16b expression plasmid (six histidines followed by an EcoRI site then the BamHI site) in frame with the histidine Tag sequence. The resulting plasmids were transformed into *Escherichia coli* BL21 cells using standard protocols and protein expression induced using IPTG. The insoluble recombinant proteins in the form of inclusion bodies were extracted from bacterial cells by multi-phase sonication in a buffer consisting of 2M urea, 20 mM Tris-HCl, 0.5 M NaCl and 2% Triton X-100 at a pH of 8.0. The resulting proteins were solubilized over the course of one hour in a buffer consisting of 6 M guanidinium hydrochloride, 20 mM Tris-HCl, 0.5 M NaCl, 10 mM imidazole and 1 mM 2-mercaptoethanol at a pH of 8.0. Target proteins were purified by His Tag binding affinity chromatography on Chelating Sepharose Fast Flow columns, previously charged with $NiSO_4$. A one hour linear gradient of 6 M to 0 M urea, at a flow rate of 0.4 ml/min was used to refold the target proteins on the affinity matrix. Elution using a buffer containing 20 mM Tris-HCl, 0.5 M NaCl, 0.5 M imidazole and 1 mM 2-mercaptoethanol at a pH of 8.0. followed this. Eluted material was subjected to electrophoresis on a 4-12 % NuPAGE gel and visualised by staining using Coomassie Brilliant Blue. Intensely stained purified bands were identified for protein genes SEQ ID NO: 1, 3, 5 and 11. These were further confirmed by trypsin digestion of soluble protein fractions or protein gel band isolation followed by mass spectrometry.

Digested fragments were compared to the Mass Spectrometry Data Base (MSDB) where proteins encoded by the DNA sequences of SEQ ID NO: 3, 5 and 11 (amino acid sequences provided in SEQ ID NO: 15, 17 and 23, respectively) were positively identified. The protein gene product of SEQ ID NO: 1 (amino acid sequence provided in SEQ ID NO: 13) was identified by comparison to a limited in-house database. Proteins with SEQ ID NO: 15, 17 and 23 were dialyzed against 20 mM Tris-HCl at pH 8.0. In addition, proteins with SEQ ID NO: 13, 15, 17 and 23 were also maintained in their elution state i.e. in a buffer containing 20 mM Tris-HCl, 0.5 M NaCl, 0.5 M imidazole and 1 mM 2-mercaptoethanol at a pH of 8.0.

The purified protein of SEQ ID NO: 23, encoded by SEQ ID NO: 11, was tested in the "SPLAT" assay (Smallwood et al., *Biochem. J.* 340:385-391, 1999) to investigate its impact on ice restructuring. In the sucrose-sandwich-splat assay, 2 μl of purified protein in 30% (w/w) sucrose was squashed between 13 mm circular cover slips. The 'sandwich' was dropped into a bath of heptane held at −80° C. in a box of solid $CO_2$ and transferred into a glass viewing chamber containing heptane maintained at −6° C. by a circulating cooler (Grant). Ice crystals were viewed using a 20× objective on an Optiphot microscope (Nikon) and images captured at 0 and 30 minutes incubation at −6° C. using a video camera into an image analysis system (LUCIA, Nikon). The results showed that antifreeze protein AFP5, corresponding to the product from SEQ ID NO: 11, inhibited ice recrystallization at a concentration of 0.9 and 1.8 mg/ml. The effects could clearly be observed at the initiation of the assay i.e. time=zero minutes, but were far more pronounced at the thirty-minute interval. At this point the ice crystals formed using the 20 mM Tris-HCl control were many fold larger than the ice crystals formed in the presence of AFP5 at either 0.5 or 1.0 mg/ml. AFP5 also displayed a concentration effect where the ice crystals formed at the higher concentration were smaller than those that propagated at the lower concentration.

As the SPLAT assay is performed in 30% sucrose, these results also showed that APF5 is able to modify sucrose solutions.

EXAMPLE 4

Use of Grass Anti-Freeze Protein Genes to Change Ice Crystal Size in Simple, Non-Sucrose, Solutions To obtain soluble, recombinant, fusion proteins, the grass genes were amplified by PCR with the primers as described above in Example 3. These PCR fragments were cloned in-frame with the NusA fusion protein in the pET44 series of vectors (Novagen). Soluble fusion protein was obtained by expression in *E. coli* BL21 (DE3) pLysS cells (Novagen), for AFP proteins 1, 2, 3 and 5 and the truncated version of AFP1 (designated AFP1b). Fusion proteins were purified by His-tag binding affinity chromatography on Chelating Sepharose Fast Flow columns, previously charged with $NiSO_4$. The eluted protein was dialyzed against 20 mM Tris pH8 using VivaSpin (VivaScience, Hanover, Germany) 5 kDa cut-off columns.

Proteins without the NusA-tag (His-tag only) were prepared essentially as described in Example 3, however, during the refolding process, 0.5 M L-Arginine was added to increase stability and recovery. The resulting proteins were dialyzed against 20 mM Tris pH8.

Proteins were tested for ice-recrystallization inhibition activity in 20 mM Tris using a SPLAT assay as described below. NusA-tagged and His-tagged proteins of AFP 1, 1b, 2, 3 and 5 were quantified using Bradford reagent and quantitative polyacrylamide gel. Ten-fold serial dilutions of the proteins were prepared in 20 mM Tris from 10 µg/ml to 0.01 µg/ml of protein. Tris buffer and BSA were used as negative controls.

Thin slices of flash-frozen sample were prepared by dropping approximately 10 µl of sample from a height of 3 m onto a polished metal block cooled to −78° C. A suitable sized sample of minimum thickness was excised, sandwiched between two cover slips and transferred to a microscope stage, cooled by ethanol from a refrigerated circulator (Haake F3Q), held at −20° C. The stage was warmed up to −8° C. over 1 minute and held constant at this temperature for 30 minutes. The sample was viewed using a Zeiss Axiophot Photomicroscope with a 10× objective lens and a 10× eyepiece. Photographs were taken using a Sony DSC-S75 Cybershot digital camera and correct distances were calibrated using a graticule. The images were analyzed using MetaMorph software (Universal Imaging Corp., Westchester, Pa.) and accurate crystal sizes determined for each sample. The diameters of the ten largest crystals were measured on a Macintosh computer using the public domain Image J program (version 1.33 u; Rasband, W. S. (1997-2005). National Institutes of Health, Bethesda, Md.). The average of the diameters of ten crystals was used as a measure of ice re-crystallization inhibition activity.

All of the His-tagged AFPs were able to significantly reduce ice re-crystallization (inhibit crystal growth) at very low concentrations. FIG. 14 shows the activity of the His-tagged AFPs. These results show that all of the AFPs have a comparable activity with the exception of AFP1, which shows slightly lower activity. However, this may reflect the fact that AFP1 recombinant protein was more unstable than the other proteins.

Figure 15:
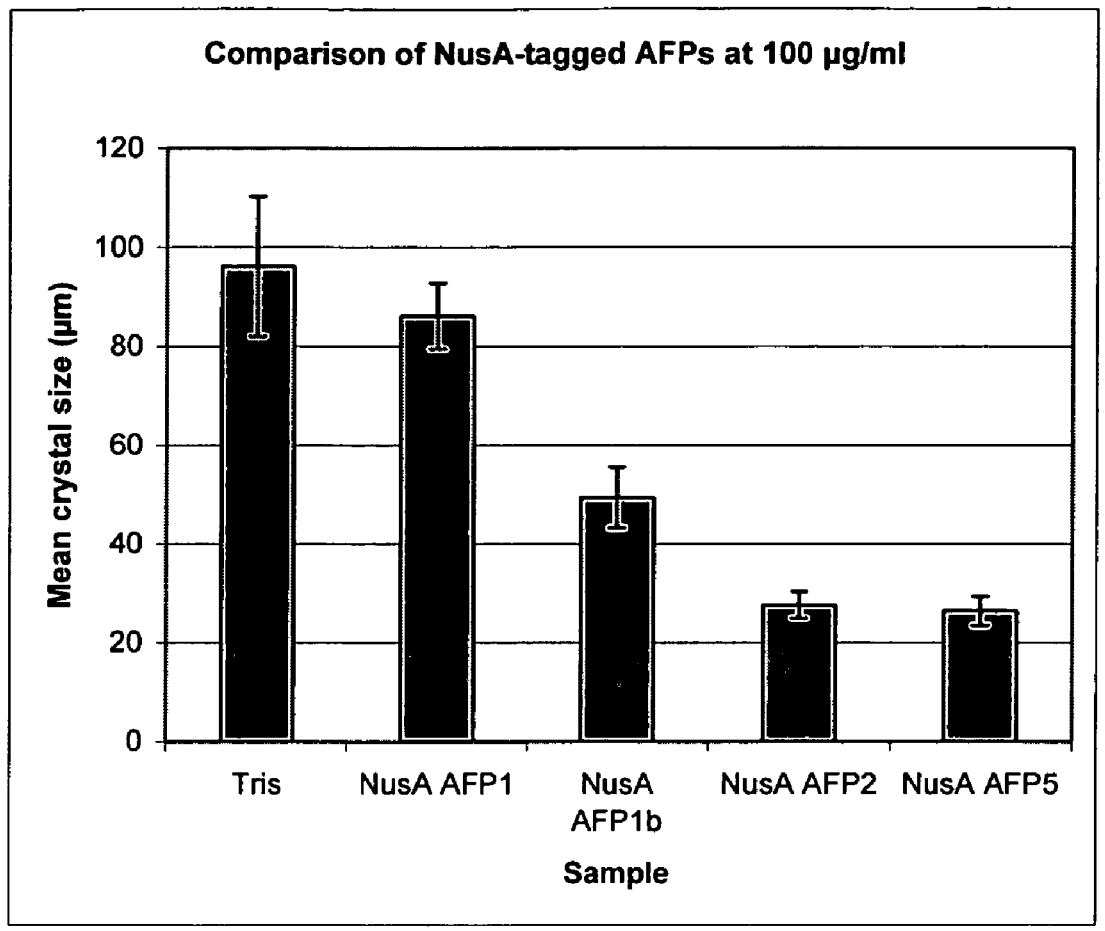
FIG. 15 shows ice re-crystallization inhibition activity of NusA-tagged AFP1, AFP1b, AFP2 and AFP5 at a protein concentration of 100 µg/ml. Standard deviations from the mean are shown.

The NusA-tagged proteins showed varying levels of activity compared to the His-tagged proteins. At 100 µg/ml, the His-tagged AFP2 and 5 reduced crystal size to ~20 µm, shown in FIG. 15. NusA:AFP1b had lower activity and NusA:AFP1 had little, if any, activity. Therefore, in some cases the large NusA protein affects ice re-crystallization inhibition activity.

Figure 16:
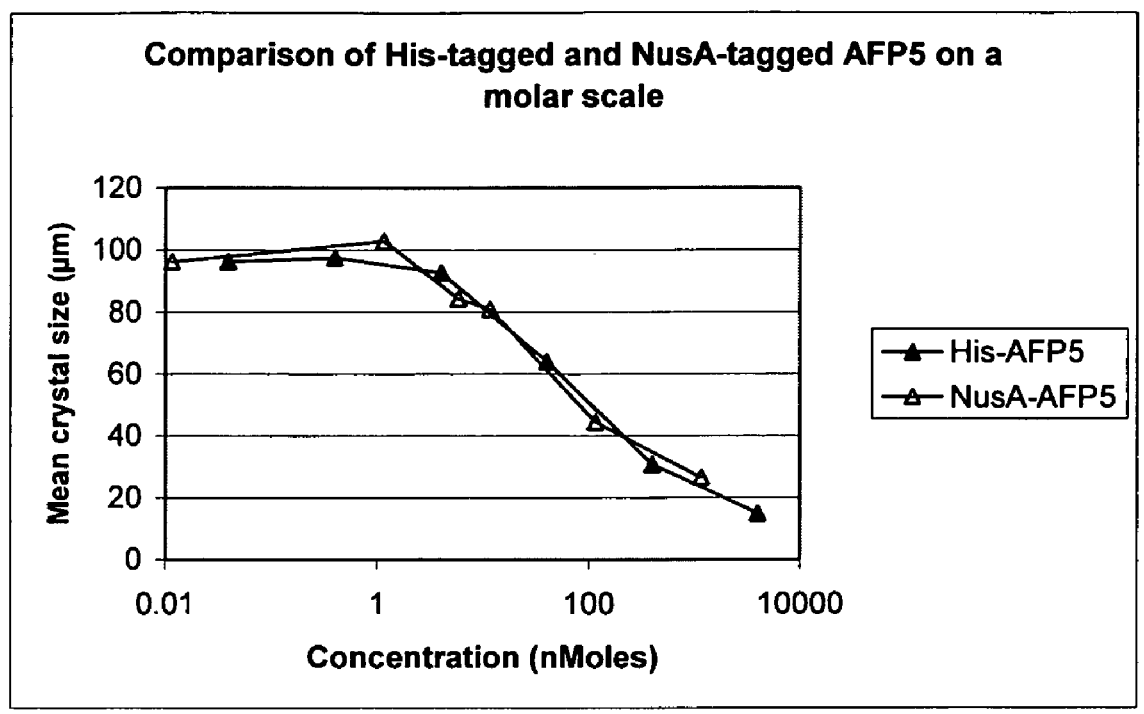
FIG. 16 shows ice re-crystallization inhibition activity of the NusA-tagged and His-tagged AFP5. Data is represented on a molar scale.

A comparison of His-tagged AFP5 and NusA:AFP5 showed that the His-tagged protein had greater activity at each protein concentration tested. However, when this data was represented as activity on a molar scale, the two proteins had similar activity (FIG. 16). This suggests that the activity is a function of the number of molecules present, and may indicate the presence of an ice re-crystallization inhibition domain.

These results show that AFP1, 2, 3, and 5 alter crystal size at low concentrations (1 ppm) and that the NusA recombinant protein can also be used to gain this affect.

EXAMPLE 5

Use of Grass Anti-Freeze Protein Genes to Reduce Drying Time

Antifreeze proteins AFP2, AFP3 and AFP5 corresponding to the products from SEQ ID NOS: 3, 5 and 11 (amino acid sequences provided in SEQ ID NO: 15, 17 and 23, respectively) were tested for their ability to increase the rate of drying of liquids in a SpeedVac™ vacuum concentrator set at medium heat. After dialysis against 20 mM Tris-HCl pH 8.0, the concentration of Tris-HCl was adjusted to 8 mM. AFPs in Tris buffer were pipetted into 1.5 ml eppendorf tubes such that each tube contained 500 µl of liquid. Antifreeze proteins were in the range of 0.1 µg to 200 µg in 500 µl volumes. Controls of either 500 µl 8 mM Tris or 500 µl MilliQ water were used. AFP2 and AFP3, at a concentration of 20 to 100 µg/ml facilitated rapid drying of 500 µl of 8 mM Tris-HCl in 75 minutes. Controls remained at volumes of 200-300 µl after 4 hours of vacuum drying. AFP5 at a concentration of between 100 and 400 µg/ml reduced in volume to approximately 20-50 µl after 4 hours. This compared favorably to controls, which had volumes of 200-300 µl after 4 hours.

Figure 17:
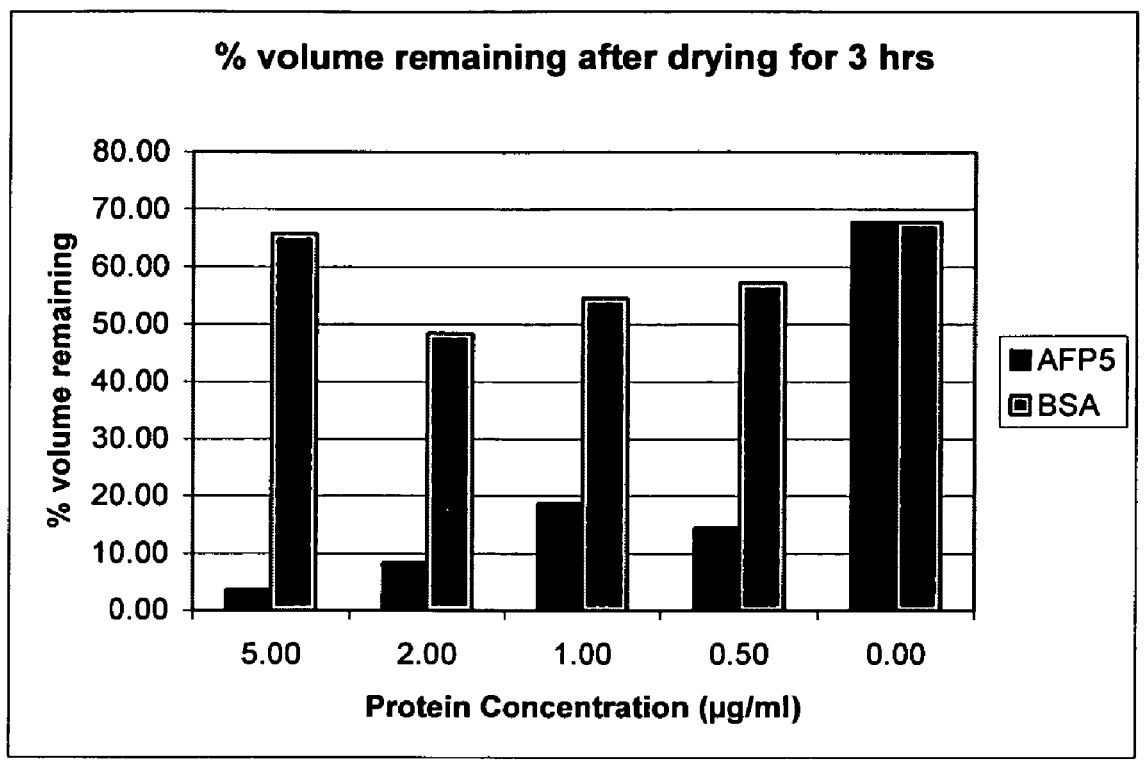
FIG. 17 shows the effect of His-tagged AFP5 on the drying rate of a simple Tris buffer solution in a SpeedVac. Data shows the percentage of the liquid remaining after drying for 3 hours under these conditions.

To further verify these results, experiments were repeated as above and replicated 10 times. The volume dried was determined by weight. FIG. 17 shows the affect of AFP5 on drying rate of a 20 mM Tris solution. BSA of the same concentration was used as a control. The results show that AFP5 has an effect on drying rate at concentrations down to at least 0.5 µg/ml.

Figure 18:
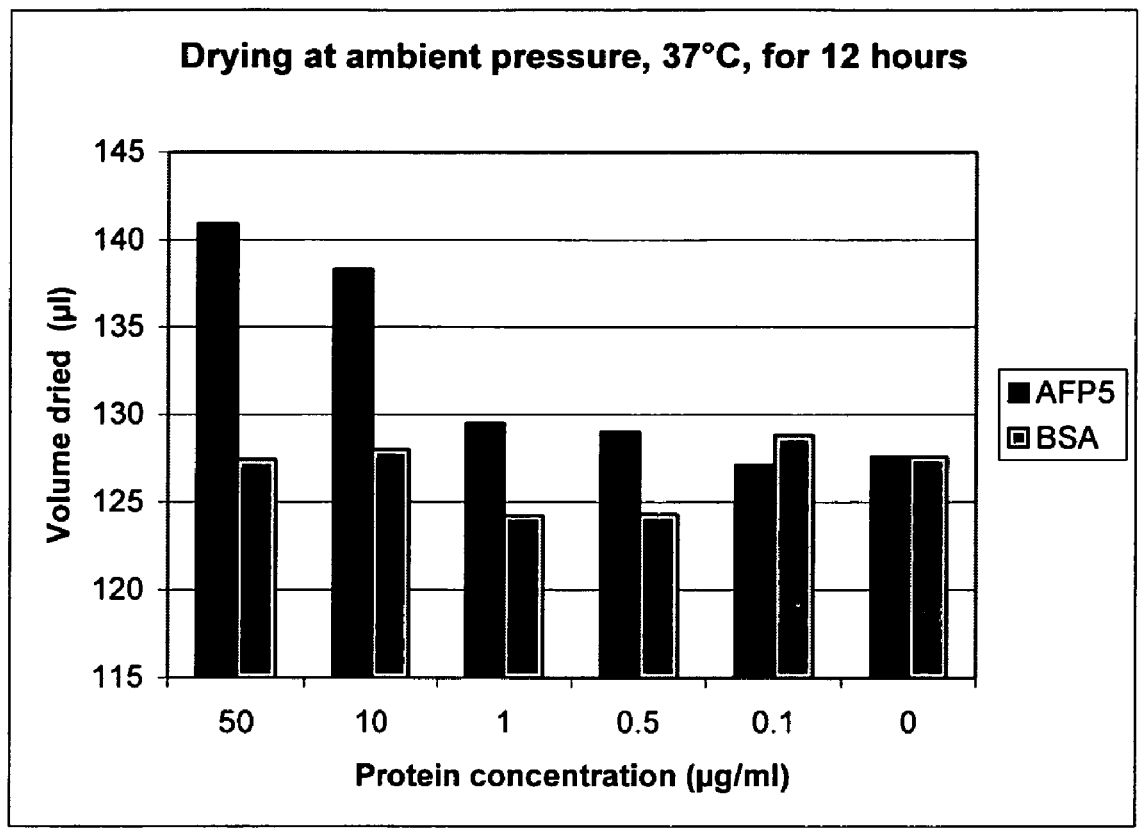
FIG. 18 shows the effect of His-tagged AFP5 on the drying rate of a simple Tris buffer solution at ambient pressure and 37° C. for 12 hours.

To determine the effect of AFP on the drying rate at ambient pressure, experiments were repeated as above but drying was carried out in an incubator, with air flow at 37° C., at ambient pressure for 12 hours. FIG. 18 shows that, even at ambient pressure, AFP5 has an effect on drying rates of the Tris buffer, but this effect is reduced in comparison to the low pressure conditions of the SpeedVac.

Further experiments showed that the His-tagged AFP5 can be dried, stored and re-used. Drying experiments were set up in the SpeedVac as before and solutions of AFP5 were completely dried. After storage for several days, the protein was reconstituted with water and the drying experiments were repeated with Tris control. The drying rate of the AFP5 solution was comparable with fresh AFP5.

These results demonstrate that AFP5 used as an additive reduced the drying time significantly. This effect is seen at both low pressures and at ambient pressures. The findings also show that AFP5 may be dried and stored before use.

EXAMPLE 6

Figure 19:
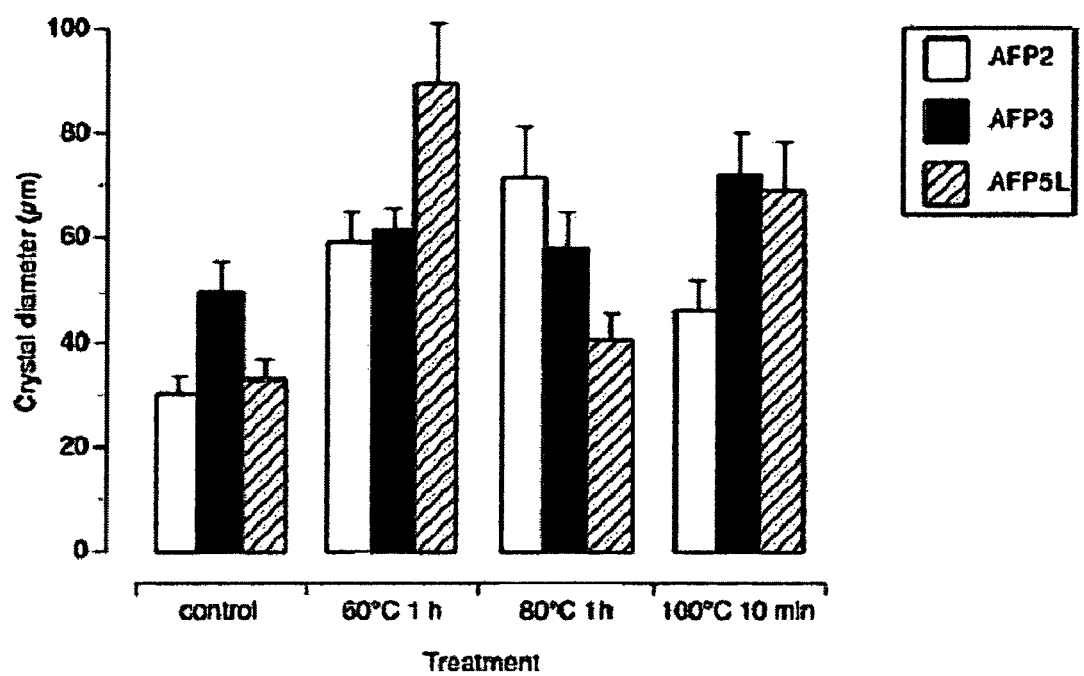
FIG. 19 shows the effect of heat treatment on the ice re-crystallization inhibition properties of the expressed AFP2, AFP3 and AFP5L proteins.

Effect of Heat Treatment on the Re-Crystallization Inhibition Properties of the Antifreeze Proteins Antifreeze proteins AFP2, AFP3 and AFP5L corresponding to the products from SEQ ID NOS: 3, 5 and 10 (amino acid sequences provided in SEQ ID NO: 15, 17 and 22, respectively) were subjected to heat treatment followed by a SPLAT freezing assay to determine the effect of heat treatment on the re-crystallization inhibition (RI) properties of the expressed proteins. The proteins were subjected to heat treatment in a 50 µl sample volume at a concentration of 0.015 mg/ml in a heating block, with a layer of oil on the surface of the sample to prevent evaporation. Heat treatments were at 60° C. for 1 hour, 80° C. for 1 hour and 100° C. for 10 min, as well as an unheated protein control. The samples were then assayed for RI using the SPLAT freezing assay as described in Example 4. The results indicate some heat tolerance in each of the proteins, as shown in FIG. 19.

EXAMPLE 7

Determination of the Thermal Hysteresis Activity and Binding of Antifreeze Proteins to the Ice Crystals Nanolitre osmometry is used to determine the osmolality of a solution to measure the effect of an antifreeze protein on ice crystal shape and the degree of thermal hysteresis or antifreeze activity. Antifreeze proteins AFP2, AFP3 and AFP5L (0.15 mg/ml) corresponding to the expressed gene products from SEQ ID NOS: 3, 5 and 10 (amino acid sequences provided in SEQ ID NO: 15, 17 and 22, respectively) were treated to determine the effect on the osmolality of the solution as described by Wharton et al., *Cryobiology* 51:198-207 (2005) and Zachariassen et al., *Cryobiology* 44:132-141 (2002). The control used in this experiment was buffer containing no AFP. The results of the nanolitre osmometry are listed in Table 3.

TABLE 3

| Sample | No. | Melting Point ° C. | Osmolality (mOsm) | Mean | SE | Hysteresis freezing point ° C. | Hysteresis ° C. | Mean | SE | Crystal shape |
|---|---|---|---|---|---|---|---|---|---|---|
| AFP2 | 1 | −0.06 | 32 | 64.3 | 20.4 | −0.1 | 0.04 | 0.03 | 0.01 | Hexagon |
| | 2 | −0.11 | 59 | | | −0.13 | 0.02 | | | Hexagon |
| | 3 | −0.2 | 102 | | | −0.23 | 0.0 | | | Hexagon |
| AFP3 | 1 | −0.33 | 172 | 107.7 | 32.7 | −0.36 | 0.03 | 0.02 | 0.01 | Weak hexagon |
| | 2 | −0.13 | 65 | | | −0.15 | 0.02 | | | Weak hexagon |
| | 3 | −0.17 | 86 | | | −0.18 | 0.01 | | | Weak hexagon |
| AFP5L | 1 | −0.09 | 48 | 44.7 | 3.3 | −0.11 | 0.02 | 0.03 | 0.01 | Hexagon |
| | 2 | −0.09 | 48 | | | −0.11 | 0.02 | | | Hexagon |
| | 3 | −0.07 | 38 | | | −0.11 | 0.04 | | | Hexagon |
| Buffer | 1 | −0.09 | 48 | 43 | 2.9 | −0.12 | 0.03 | 0.03 | 0 | Disc |
| | 2 | −0.07 | 38 | | | −0.1 | 0.03 | | | Disc |
| | 3 | −0.08 | 43 | | | −0.1 | 0.02 | | | Disc |

These results show that AFP2, AFP3 and AFP5L have little or no thermal hysteresis activity. This assay also showed that AFP2 and AFP5L produce a hexagonal crystal form, which indicates binding of the protein to the ice crystal (Griffith and Ewart, *Biotech. Advances* 13:375-402, 1995).

SEQ ID NO: 1-44 are set out in the attached Sequence Listing. The codes for nucleotide sequences used in the attached Sequence Listing, including the symbol "n," conform to WIPO Standard ST.25 (1998), Appendix 2, Table 1.

All references cited herein, including patent references and non-patent publications, are hereby incorporated by reference in their entireties.

While in the foregoing specification this invention has been described in relation to certain preferred embodiments, and many details have been set forth for purposes of illustration, it will be apparent to those skilled in the art that the invention is susceptible to additional embodiments and that certain of the details described herein may be varied considerably without departing from the basic principles of the invention.

We claim:

1. An isolated polynucleotide comprising SEQ ID NO: 3.

2. An isolated polynucleotide comprising at least one of
   (a) a sequence having at least 95% identity to SEQ ID NO: 3; and
   (b) a sequence having at least 98% identity to SEQ ID NO: 3;

wherein the polynucleotide encodes a polypeptide capable of at least one of:

i) reducing the size of ice crystals formed in a plant during freezing, and ii) increasing freezing tolerance in a plant, compared with a plant that does not express the polypeptide, and wherein the polypeptide comprises a seven amino acid repeat sequence X X N X V X G, wherein X equals any amino acid.

3. An isolated polynucleotide that encodes SEQ ID NO: 15.

4. A genetic construct comprising the polynucleotide of any one of claims 1, 2 and 3.

5. A transgenic cell comprising the genetic construct according to claim 4.

6. A genetic construct comprising, in the 5'-3' direction:
   (a) a gene promoter sequence;
   (b) the isolated polynucleotide of any one of claims 1, 2 and 3; and
   (c) a gene termination sequence.

7. The genetic construct of claim 6 wherein the polynucleotide is in a sense orientation.

8. A transgenic cell comprising the genetic construct of claim 6, wherein the cell does not form part of a human.

9. A plant, or progeny thereof, comprising a transgenic cell that comprises the genetic construct of claim 6.

10. A method for modulating increasing cold tolerance in a plant, comprising stably incorporating into the genome of the plant at least one polynucleotide of any one of claims 1, 2 and 3 and expressing the polynucleotide in the plant, thereby increasing cold tolerance in the plant.

11. A method for increasing cold tolerance in a plant comprising stably incorporating into the genome of the plant a genetic construct comprising:
   (a) a gene promoter sequence;
   (b) the isolated polynucleotide of any one of claims 1, 3 and 10; and
   (c) a gene termination sequence;
   and expressing the polynucleotide in the plant, thereby increasing cold tolerance in the plant.

12. A method for producing a plant having increased cold tolerance, comprising:
   (a) transforming a plant cell with the genetic construct of claim 6 to provide a transgenic cell; and
   (b) cultivating the transgenic cell under conditions conducive to regeneration and mature plant growth,
   thereby producing a plant having increased cold tolerance.

13. The method of claim 12 wherein the plant is selected from the group consisting of: *Lolium species: Festuca species*; and *Eucalyptus* species.

14. A method for increasing the activity of an antifreeze protein in a plant comprising stably incorporating into the genome of the plant the genetic construct of claim 6 and expressing the polynucleotide in the plant, thereby increasing the activity of the antifreeze protein in the plant.

* * * * *

UNITED STATES PATENT AND TRADEMARK OFFICE
CERTIFICATE OF CORRECTION

| | | |
|---|---|---|
| PATENT NO. | : 7,968,767 B2 | |
| APPLICATION NO. | : 11/594324 | |
| DATED | : June 28, 2011 | |
| INVENTOR(S) | : Jeroen Demmer et al. | |

It is certified that error appears in the above-identified patent and that said Letters Patent is hereby corrected as shown below:

| Col. No. | Line(s) | Edits |
|---|---|---|
| 75 | 12 | Replace "A method for modulating increasing" with --A method for increasing-- |
| 76 | 2 and 3 | Replace "the isolated polynucleotide of any one of claims 1, 3 and 10" with --the isolated polynucleotide of any of claims 1, 2 and 3-- |

Signed and Sealed this
Thirteenth Day of March, 2012

David J. Kappos
*Director of the United States Patent and Trademark Office*

SEQUENCE LISTING

<160> NUMBER OF SEQ ID NOS: 44

<210> SEQ ID NO 1
<211> LENGTH: 841
<212> TYPE: DNA
<213> ORGANISM: Lolium perenne

<400> SEQUENCE: 1

```
ggatggtttg tgtatggata tatcatatat agcataccgc agctagctca gtccatggcg      60
aaatgctggc agctgctgct cttcttggca ctcctcttgc cggcggcgag cgccgcgtcg     120
tgccaccctg atgacctcta tgccctgcgg gacttcgccg gcaacctcag aggcgggggc     180
gtcctcctcc gcgccgcctt gcccggcgcc tcgtgctgcg gctgggaagg tgtgggctgc     240
gacggcgcaa gcggctgcgt caagagcttc agatattgc tcaaagggct caccgccgct     300
ggccgttcac tgggtaaggc gttcactcac atgccattac atgtgaagcc tagccaagga     360
acactcgacg aagaccacaa tacaataact gggatcaaca atactgtcag atccgggagc     420
aacaatgttg tttctgggaa cgataacact gtcatatccg gaacaacaa cgtcgtgtcc     480
gggagccaca acaccgtcgt atttgggggt gacaacttca taagtggaag ttaccatgtc     540
gtatctggga accaccatgt tgtgactgac aacaagaatg ccgtatccgg ggaccacaat     600
actgtatctg gaagccaaaa taccgtatcc gggaaccacc agatcgtatc tgggagccac     660
agtaccgtat ccgggaacca caatacggta tctgggagaa caattccgt atatgggaac     720
aacaatattg tatctgggag caaccatgtt gtatatggga acaacaaagt cgtgacagga     780
ggttaataat ctgtcactag attgttttaa tgcatcttct cggttcagtg taaaaaaaaa     840
a                                                                    841
```

<210> SEQ ID NO 2
<211> LENGTH: 959
<212> TYPE: DNA
<213> ORGANISM: Festuca arundinacea

<400> SEQUENCE: 2

```
ggcgacactt gcttggattc caatcaaggt ttcgtgctgg tttgtgtatg gatatatagc      60
ataccgcagc tagctcaatt catggcaaaa tgctggcagc tgctactctt cttggcattc     120
ctcttgccgg cggcgagcgc cgcgtcacgc caccctgatg acctccgcgc cctgcaggac     180
ttcgccggca acctcagagg cgggggcgtt gtcctccgcg ccgccttgtc cggcggctca     240
tgctgcgact gggaaggtgc gggctgcgac ggtgcaagtg gccgcgtcac gagtttccag     300
atattgctca aagggctcac caccgctggc cgttcactgg gtaaggcgtt cactaacatg     360
ccattacatg tgaagtctag ccaaggaaca ctcgacgaag aacacaatac aataactggg     420
atcaacaata ctgtcaaatc cgggagcaac aatgttgttt ctgggaacga taacactgtc     480
atatccggga caacaacgt cgtgtccggg agccacaaca ccgtcgtatt tgggggtgac     540
aatttcctaa gcgtagcaa ccatgtcgta tctgggaacc accatgtcgt gactgacaac     600
aagaatgccg tatccgggga ccacaatact gtatctggaa gccaaaatac cgtatccggg     660
aaccaccata tcatatctgc gagccacagt accatatccg ggaaccacaa taccgtatcc     720
gggagcaaca atttcgtatc tgggacaac aatattgtat ctgggagcaa ccatgtcgta     780
tatgggaaca acaaggtggt gacaggaggt taataatttg tcactggatt gtttccatgc     840
```

| atgttctcgg ttcagtgtag ctcacgatca cttggtgggg ccaatcacgt tatgtaactt | 900 |
| catgtaagca taattttttcg tgcttttaat aaaacttccc tacagataaa aaaaaaaaa | 959 |

<210> SEQ ID NO 3
<211> LENGTH: 980
<212> TYPE: DNA
<213> ORGANISM: Lolium perenne

<400> SEQUENCE: 3

| gcttgcattc caatcaaggt ttcttgttca atccatgcct gaatacatgg caaagtgttg | 60 |
| catgctgctg gtcttcttgg ggttcatctt gcaggtggca ggagcaacgt cgtggtcgtg | 120 |
| ccaccacgac gacctccacg cgttgagggg cctcgctgag aacctaagcg gcaaaggagc | 180 |
| cgtccgcctc cgcgccgcat ggtccggcgc ctcatgctgc agctgggaag gtgtgggatg | 240 |
| cgaaacagca agcggccgcg tcgtggcgtt gcggctcccc aagcgcggcc ttggagggat | 300 |
| catcccatcg tcgattggtg agcttgatca ccttcgctat ttggatctct cgggtaattc | 360 |
| attggttggg gaggtaccaa aaagtttgca gatacggctc aagagcctca ccactgacag | 420 |
| ccagtcactc ggtatgggtt ccattaacat gctattgcat gtgagcagta aagaacgct | 480 |
| cgatgaagaa ccaaatacaa tatcagggac caacaatagt gttggatcag ggagcaacaa | 540 |
| tgttgtttcc gggaatgaca acacggtcgt atctgggaat aacaaccatg tgtctgggag | 600 |
| caacaacact gttgtaactg gaagtgacaa tactgtagtt ggtagcaacc atgtcgtatc | 660 |
| agggacaaag catattgtta ctgataacaa taatgttgta tccgggaacg acaataatgt | 720 |
| gtctggaagc ttccatactg tatcagggga gcacaatacc gtatccggga gcaacaatac | 780 |
| tgtatccggg agcaaccata tcgtatctgg gagcaacaaa gtcgtaacag atggttaata | 840 |
| ttctgtaggt gcaggattgc ttccatcttc ccaagttcag tgtagcttac aatcaataga | 900 |
| tggagacaat cacgttatgt aacttcagga tatggcatac ttttcctta aataaagctt | 960 |
| ccctttacat aaaaaaaaaa | 980 |

<210> SEQ ID NO 4
<211> LENGTH: 996
<212> TYPE: DNA
<213> ORGANISM: Festuca arundinacea

<400> SEQUENCE: 4

| gacatagctt gcattccaat caaggtttct tgttcaatcc atgcctgaat acatggcaaa | 60 |
| gtgttgcatg ctgctgctcc tcttggcctt catcctcttg caggtggccg gagcaacgtc | 120 |
| gtggtcgtgc caccacgacg acctccgcgc attgagggc ttcgccgaga acctaagcgg | 180 |
| caaaggagcc gtccgcctcc gcgccgcatg gtccggcgcc tcatgctgca gctgggaagg | 240 |
| tgtgggatgc gaaacagcaa gcggccgcgt cgcggcgttg cggctcccca agcgcggcct | 300 |
| tggagggacc atcccatcgt cgattggtga gcttgatcac cttcgttgtt tggatctctc | 360 |
| gggtaattca ttggttggga aggtaccaaa aagtttgcag atacggctct agagcctctc | 420 |
| cactgatggc cagtcactcg gtatgggttc cattaacacg ctattgcatg tgagcagtaa | 480 |
| cagaagaacc ctcgatgaag aaccaaatac aatatcaggg accaacaata gtgttggatc | 540 |
| agggagcaac aatgttgttt ccgggaatga caacacggtc atatctggga ataacaacca | 600 |
| tgtgtctggg agcaacaaca ctgttgtaac tggaagtgac aacactttag ttggtagcaa | 660 |
| ccatgtcgta tcagggacaa agcatattgt tactgataac aataatgttg tatccgggaa | 720 |
| cgacaataat gtgtctggga gcttccatac tgtatcaggg gagcacaata ccgtatctgg | 780 |

```
gagcaacaac actgtatccg ggagcaacca tgtcgtatct ggaagcaaca aagtcgtaac    840
agatggttaa tattctgtag gtgcaggatt gcttccatct tcccaagttc agtgtagctc    900
ataatcaatt gatggagaca atcacgttat gtaacttcag gatatggcat acttttcctt    960
taaataaagc ttccctttac ataaaaaaaa aaaaaa                              996
```

```
<210> SEQ ID NO 5
<211> LENGTH: 1084
<212> TYPE: DNA
<213> ORGANISM: Lolium perenne

<400> SEQUENCE: 5
gacttgcatt ccaaaaaggt ttcttgcata cacgtattta gaacaccaga acttaatcca     60
tggcgaaatg ttggctgctg ctgctcttct tggtgttcct cttgctggcc atgagcgcga    120
cgtcgtgcca cctggatgac ctccgcgcgc tgcggggctt tgtcgggaac ctcaatggcg    180
ggggtgccct tctccgtgga acatggtctg gctcctcatg ctgcgattgg aaggtgtgg    240 gctgcgatgg tacaagcggc cgcgtcacgg cgttgcggct tccgattagc ctcgaggact    300
gcggtaagct caagtcgctc aaccttgcca acgaaagatt ggttggcacc atcccgtcgt    360
ggattggtga gcttgaccac cattgctact tggttctctc ggataattca ttggttggta    420
aggcacccaa tagtttgcac aatagtttgc agataagact caagggcctc gccaccgctg    480
gtcgttcact aggtatggct ttcgctaaca tgccattgca tgtgaagggg aaccgaagaa    540
ccctcgacga caaacaaat acaatacatg ggaccaacaa cactgttaga ctgggaacg    600 acaatgctgt ttctgggaac gacaacactg tcatatgtgg gaacaacaac actgtgtctg    660
ggagcaacaa caccattgca tctggcagtg acaatatcgt aactggcagc aaccatattg    720
tatgtgggac caaacatatc ataactgata caacaatga cgtatccggc aatgataata    780
atgtatctgg gagcttccat actgtatccg ggagccacaa tactgtatct ggaagtaaca    840
acactgtatc tggaagcaac catgtcgtat ctggaagcaa caaactcgtg acaggagatg    900
aatgatttgt caggggattg cttccatctt cctaaagga gctctcaccc tagtccaagt    960
tcggtgcagc tcacaatcac ttggtaggga caatcgagtt atgtaacttc atggatatag   1020
catcattctc cctgtttaaa tatacttttcc tgaaaatatc ttacataaat gctgaaaaaa   1080
aaaa                                                                1084
```

```
<210> SEQ ID NO 6
<211> LENGTH: 1230
<212> TYPE: DNA
<213> ORGANISM: Festuca arundinacea

<400> SEQUENCE: 6
actcacttgc attccaaaaa aggtttcttg ctgagttgtt tgcgtacaca taattagaac     60
accacaactc aatccatggc gaaatgttgg ctgctgctgc tcttcttggt ggtcctcttg    120
ccggccgcga gcgcgacgtc gtgccacccc gatgacctcc gcgcgctgcg tggctttgtc    180
gggaacctca atggcggggg tgtccttctt catggagcat ggtccggctc cttatgttgc    240
gcctgggaag gcgtgggctg cgatggtaca agcggccgcg tcacggcatt gcggcttccg    300
attagcctca aggattgcgg caagctcaag tcgctcaacc ttgccaacga tagactggtt    360
ggcaccatcc cgtcgtggat tggtgagctt gaccaccttt gctacttggt tctctcggat    420
aattcattgg ttggtaaggt acccaatagt ttgcagataa gactcaaggg cctcgccacc    480
gctggtcgtt cactaggtat ggctttcgct aacatgccat tgcatgtgaa gggcaaccga    540
```

| | |
|---|---|
| agaacactcg acgaacaaac aaatacaata caggggacca acaacacagt tagatctggg | 600 |
| aacgacaatg cagtttctgg gaacgacaac actgtcatat gtgggaacaa caacactgtg | 660 |
| tctgggagca acaatactat tgtatctggg agtgacaata tcgtaactgg tagcaaccag | 720 |
| gttgtatgtg ggaccaaaca tatcataact gataacaaca atgacgtatc cgggaacgat | 780 |
| aacaatgtat ctggagttc ccatactgta tccgggagcc acaatactgt atccggagt | 840 |
| aacaacactg tatctggaag caaccatgtc gtatctggga gcaacaaagt cgtgacagga | 900 |
| gatgaatgat tgtcaggggg atcgtttcca tcttccctaa aggagcactc acccttgtcc | 960 |
| aagttcagtg tagctcacag tcacttggta gggacaatcg agttatgtaa cttcatggat | 1020 |
| atagcctcat ttttctagtt taaatatact ttcctgaaaa tatcttacat acatgctgat | 1080 |
| ataaatataa aggcggcttt catgctactg atgtatacca agcgtgtttt cttgtgtacg | 1140 |
| aatttgcatg gacatgcagc tgatgtagac caagcgtgtt atatgtgata tgtgatgctt | 1200 |
| taataaacat atttttgttg aaaaaaaaaa | 1230 |

<210> SEQ ID NO 7
<211> LENGTH: 1212
<212> TYPE: DNA
<213> ORGANISM: Lolium perenne

<400> SEQUENCE: 7

| | |
|---|---|
| gcttgcattc caaaaaggtt tcttgcgtac acgtatttag aagaccacaa cttaatccat | 60 |
| ggcgaaatgt tggctgctgc tgctcttctt ggtgttcctc ttgctggccg tgtgcgcgac | 120 |
| atcgtgccac ccagatgacc tccgcgcgct gcggggcttt gtcgggaacc tcaatggcgg | 180 |
| gggtgtcctt ctccgtgaaa catggtctgg ctcctcatgc tgcgcctggg aaggtgtggg | 240 |
| ctgcgatggt acaagcggcc gcgtcacggc gttgcggctt ccgattagcc tcgaggattg | 300 |
| cggtaagctc aagtcgctca accttgccaa cgaaagattg gttggcacca tcccgtcgtg | 360 |
| gattggtgag cttgaccacc attgctactt cgttctctcg acaattcat tggttggtaa | 420 |
| ggtacccaat agtttgcaga taagactcaa aggcctcgcc accgctggtc gttcactagg | 480 |
| tatgctttc gctaacatgc cattgcatgt gaagggggaac cgaagaacac tcgacgaaca | 540 |
| aacaaataca atacatggta ccaacaaac tgttagatct gggaacgaca atgctgtttc | 600 |
| tgggaacgac aacacagtca tgtgtgggaa caacaacaca gtgtctggga gcaacaacac | 660 |
| catttcatct ggcagtgaca atatcgtaac tggtagcaac catattgtat gtgggaccaa | 720 |
| acatatcata actgataaca acaatgacgt atccggcaat gataacaatg tatctgggag | 780 |
| cttccatact gtatccggga gccacaatac tgtatctggg agtaacaaca ctgtatctgg | 840 |
| aagcaaccat gtcgtatctg gaagcaacaa agtcgtgaca ggagatgaat gatttgtcag | 900 |
| gggattgttc catcttccct aaaggagctc tcacccttgt ccaagttcag tgcagctcac | 960 |
| aatcacttgg tagggggcaat cgagttatgt aacttcatgg atatagcatc attttcctat | 1020 |
| agtttaaata tattttcctg aaaatatctt acatacatgc tgatatgaat atcaaaggcg | 1080 |
| gctttcacgc agctgatgta tacgtgtttt cttatgtacg aatttgcatt gacatgcaga | 1140 |
| gctgatgtag accaagcttg ttctatgtaa tatgtgatgc attaaacata ttttgttga | 1200 |
| ataaaaaaaa aa | 1212 |

<210> SEQ ID NO 8
<211> LENGTH: 1064
<212> TYPE: DNA
<213> ORGANISM: Lolium perenne

```
<400> SEQUENCE: 8
gcacttactt gcattctaaa ataggtttct tgcataccac aactagctga atccatgggg      60
ctgttgctgc tcttcttggc gttcctcttg ccagtggcat gcgcggcaac gtcgagttgc     120
cacccgatg  acctccgtgc cctgcggggc tttgccaaga accttggcgg cggaggcgtc     180
ctcctccgca ccgcgtggtc cggcacctcg tgctgcgtct gggaaggtgt tggctgcaat     240
ggcgcgagcg gccgcgtcac cacgttgtgg ctccctaggc gtggccttgc ggggaccatc     300
acaggagcat ccttggccgg cctcgcgcgg ctggagtcac tcaaccttgc caacaacaga     360
ctggtcggca ccatcccatc gtggattggt gagcttgacc accttctcta cttggatctc     420
tcacataatt cattggttgg cgagctgccc aacctcaagg gcctcaccac cacaggtcat     480
ttactaggta tggctttcac tagcatgcca ttggatgtga agcctaacag aagaactctc     540
gccgtacaac caaatacaat atctgggacc aacaactcgg tcttatctgg gcgaaacaat     600
actgtgtctg ggaatgacaa cactgtcata tcggggaaca acaatactgt gtctgggagc     660
ttcaacaccg tcgtaacggg aagtgacaat gtcttaactg ggagcaacca tgtcgtatct     720
gggagaaacc atattgtaac tgacaacaac aatgctgtat ctggggacga caataatgtg     780
tccgggagct tccataaagt atctggaagt cacaatacgg tatctgggag caacaatacc     840
gtatccggga gaaaccatgt cgtatctggg agcaacaaag tcgtgacagg aggttaatga     900
tatgttagtg gattgtttcc atcttcccta agggatctca cgtacttgac aaagttcagt     960
gtagcactca atcacttggt ggggacaatc gggttatgta acgtcatgga tatagcatac    1020
gtactttttcc tactttaaat aagaactttc ctataaaaaa aaaa                    1064

<210> SEQ ID NO 9
<211> LENGTH: 1246
<212> TYPE: DNA
<213> ORGANISM: Festuca arundinacea

<400> SEQUENCE: 9
gcttacttgc attctaaaat aggtttcttg cataccacag ctagctgaat ccatggggct      60
gttgctgctc ttcttggggt tcctcttgcc agcagcgtgc gcggcaacgt cgagttgcca     120
ccccgatgac ctccgtgccc tgcggggctt gccaagaac  gttggtggcg gaggcgtcct     180
cctccgcacc gcgtggtccg gcacctcgtg ctgcgtctgg gaaggtgttg gatgcaatgg     240
cgcgagcggc gcatcaccac cgttgtggct ccctaggcgt ggccttgcgg ggaccatcac     300
aggagcatct tggccggcct cgcgaggct  ggagtcactc aaccttgcca acaacagact     360
ggtcggcacc atcccatcgt ggattggtga gcttgaccac cttctctact tggatctctc     420
acataattca ttggttggcg agctgcccaa ccgtttgcag atacggctca agggcctcac     480
caccacaggt catttactag gtatggcttt cactaacatg ccattggatg tgaagcgtaa     540
cagaagaact ctcgccatac aaccaaatac aatatctggg accaacaact ggtctttatc     600
tgggcgaaac aatgtagttt ctgggaatga caacactgtc atatcggaga caacaatac      660
tgtgtctggt agcttcaaca ccgtcataac gggaagtgac aatgtcttaa ctgggagcaa     720
ccatgtcgta tctggagaa  gccatattgt aactgacaac aacaattctg tatctgggga     780
cgacaataat gtgtccggga gcttccataa agtatccgga agtcacaata cggtatctgg     840
gagcaacaat accgtatcgg ggagaaacca tgtcgtatct gggagcaaca aaatcgtgac     900
aggaggttaa tgatatgtta gtggattgtt tccatcttcc ctaagggatc tcacgtactt     960
gacagagttc agtgtagcac tcaatcactt ggtggggaca atcggttat  gtaacttcat    1020
```

| | |
|---|---|
| gggatatatc ataccttcc tactttaaat aaaaactttc ctataatatc ttacagacct | 1080 |
| gagtatcaac agtggcttgg agctaatgta gaccaatcat atttgcttat gtacaaattc | 1140 |
| gaattgtgga tgttgacatg tggtgattat ttctcgcttt ctattctgtg cgatgtttga | 1200 |
| tgctttatta tactgattag gttgtggatc acagggaaaa aaaaaa | 1246 |

<210> SEQ ID NO 10
<211> LENGTH: 1008
<212> TYPE: DNA
<213> ORGANISM: Lolium perenne

<400> SEQUENCE: 10

| | |
|---|---|
| caacaacact tgcgagtcac ttgcattgca ggaaaggttt cttattgaat ccatctatag | 60 |
| catagcactg ctgaatccat ggcgaaatgc ttgatgctgc tgctctcctt cgcgttcctc | 120 |
| ttgtcggtgg ccggcacggc gacggcgacg ccatgccacc gcgatgacct tcgcgcgctg | 180 |
| cggggcttcg ctgagaacct gggcggcggc ggcgcaatca gcctccgcgc gcgtggtca | 240 |
| ggcgcctcat gctgcgattg gaaggcgtt ggctgcgacg gtgccagcgg ccgtgtcacg | 300 |
| gctttgtggc tccccaggag cggcctcacg gggccaatcc cgtcatggat ttgtcagctt | 360 |
| caccacctac gctacttgga tctttcaggt aatgcattgg ttggcgaggt acccaagaat | 420 |
| ctgcaggtac agctcaaagg catcaccaac atgccattgc atgtgatgcg taacagaaga | 480 |
| tcactcgacg agcagcccaa tacaatttct gggagcaaca atactgtcag atccgggagc | 540 |
| aaaaatgttc ttgctgggaa tgacaacacc gtcatatctg gggacaacaa tagtgtgtct | 600 |
| gggagcaaca acactgtcgt aagtgggaat gacaataccg taaccggcag caaccatgtc | 660 |
| gtatcaggga caaccatat cgttacagac aacaacaata acgtatccgg gaacgataat | 720 |
| aatgtatccg ggagctttca taccgtatcc gggggggcaca atactgtctc cgggagcaac | 780 |
| aataccgtat ctgggagcaa ccacgttgta tctggaagca acaaagtcgt gacagacgct | 840 |
| taatgatctg tcagcgcatg attgtttcca ccttaactga gctcacgttc ttgtccaagt | 900 |
| tcactgtacc tcacagtcag ttggtgcgtt caatcgcgtt atgtaacttc atggatatac | 960 |
| catacttttc ctactatata taaaattcc ctttacataa aaaaaaaa | 1008 |

<210> SEQ ID NO 11
<211> LENGTH: 1006
<212> TYPE: DNA
<213> ORGANISM: Festuca arundinacea

<400> SEQUENCE: 11

| | |
|---|---|
| ggcaggaaag gtttcttgtt gaatccatct atagcatagc actgctgaat ccatggcgaa | 60 |
| atgcttgatg ctgctgctct ccttcgcgtt cctcttgtcg gcggctggca cggcgacggc | 120 |
| gacgccatgc caccgggatg acctccgtgc gctgcggggc ttcgctgaga acctgggcgg | 180 |
| cggcggcgca ctcagccttc gcgccgcgtg gtcaggcgcc tcatgctgcg attgggaagg | 240 |
| cgttggctgc gacggtgcca gcggccgtgt cacggctttg tggctcccca ggagcggcct | 300 |
| cacggggcca atcccatcgt ggatttgtca gcttcaccac ctacgctact tggatctttc | 360 |
| aggtaatgca ttggttggcg aggtacccaa gaatctgcag gtacagctca aaggcctcac | 420 |
| cgctgccggt cgttcgggtt tcaccaacat gccattgcat gtgatgcgta acagaagatc | 480 |
| actcgacgag cagcccaata caatatctgg gagcaacaat actgtcagat ccgggagcaa | 540 |
| aaatgttgtt gctgggaatg acaacaccgt catatctggg gacaacaata gtgtgtctgg | 600 |
| gagcaacaac actgtcgtaa gtgggagtga caataccgta actggcagca accatgtcgt | 660 |

```
atcagggaca aaccatatcg ttacagacaa caacaataac gtatccggga acgataataa    720
tgtatccggg agctttcata ccgtatccgg ggggcacaat accgtctctg ggagcaacaa    780
taccgtatct gggagcaacc atgttgtatc tggaagcaac aaagtcgtga cagacgctta    840
atgatctgtc agcgcatgat tgtttccacc ttaactgagc tcacgttctt gtccaagttc    900
actgtacctc acagtcagtt ggtgcgttca atcgcgttat gtaacttcat ggatatacca    960 tactttcct actatatata aaatttccct taaaaaaaa aaaaaa                    1006

<210> SEQ ID NO 12
<211> LENGTH: 1007
<212> TYPE: DNA
<213> ORGANISM: Lolium perenne

<400> SEQUENCE: 12
ggagtcactt gcattgcatt gcaggaaagg tttcttattg aatccatcta tagcatagca     60
ctgctgaatc catggcgaaa tgcttgatgc tgcttctctc cttcgcgttc ctcttgtcgg    120
cggccggcac ggcgacggcg acggcgacgc catgccaccg cgatgacctt cgcgcgctgc    180
ggggcttcgc tgagaacctg gcggcggcg gcgcactcag cctccgcgcc cgtgtggtcag   240 gcgcctcatg ctgcgattgg gaaggcgttg gctgcgacgg tgccagcggc cgtgtcacgg    300 cttttgtggct ccccaggagc ggcctcacgg ggccaatccc gtcatggatt tttcagcttc   360
accacctacg ctacttggat ctttcaggta atgcattggt tggcgaggta cccaagaatc    420
tgcaggtaca gctcaaaggc atcaccaaca tgccattgca tgtgatgcgt aacagaagat    480
cactcgacga gcagcccaat acaatttctg ggagcaacaa tactgtcaga tccgggagca    540
aaaatgttct tgctgggaat gacaacaccg tcatatctgg gacaacaat agtgtgtctg    600 ggagcaacaa cactgtcgta agtgggaatg acaataccgt aaccggcagc aaccatgtcg    660
tatcagggac aaaccatatc gttacagaca acaacaataa cgtatccggg aacgataata    720
atgtatccgg gagctttcat accgtatccg ggggcacaa tactgtctcc gggagcaaca    780
ataccgtatc tgggagcaac cacgttgtat ctggaagcaa caaagtcgtg acagacgctt    840
aatgatctgt cagcgcatga ttgtttccac cttaactgag ctcacgttct tgtccaagtt    900
cactgtacct cacagtcagt tggtgcgttc aatcgcgtta tgtaacttca tggatatacc    960
atacttttcc tactatatat aaaatttccc tttacataaa aaaaaa                  1007

<210> SEQ ID NO 13
<211> LENGTH: 243
<212> TYPE: PRT
<213> ORGANISM: Lolium perenne

<400> SEQUENCE: 13

Met Ala Lys Cys Trp Gln Leu Leu Leu Phe Leu Ala Leu Leu Leu Pro
  1               5                  10                  15

Ala Ala Ser Ala Ala Ser Cys His Pro Asp Asp Leu Tyr Ala Leu Arg
                 20                  25                  30

Asp Phe Ala Gly Asn Leu Arg Gly Gly Gly Val Leu Leu Arg Ala Ala
             35                  40                  45

Leu Pro Gly Ala Ser Cys Cys Gly Trp Glu Gly Val Gly Cys Asp Gly
         50                  55                  60

Ala Ser Gly Cys Val Lys Ser Phe Gln Ile Leu Leu Lys Gly Leu Thr
 65                  70                  75                  80

Ala Ala Gly Arg Ser Leu Gly Lys Ala Phe Thr His Met Pro Leu His
                 85                  90                  95
```

```
Val Lys Pro Ser Gln Gly Thr Leu Asp Glu Asp His Asn Thr Ile Thr
            100                 105                 110

Gly Ile Asn Asn Thr Val Arg Ser Gly Ser Asn Asn Val Val Ser Gly
            115                 120                 125

Asn Asp Asn Thr Val Ile Ser Gly Asn Asn Val Val Ser Gly Ser
    130                 135                 140

His Asn Thr Val Val Phe Gly Gly Asp Asn Phe Ile Ser Gly Ser Tyr
145                 150                 155                 160

His Val Val Ser Gly Asn His Val Val Thr Asp Asn Lys Asn Ala
                165                 170                 175

Val Ser Gly Asp His Asn Thr Val Ser Gly Ser Gln Asn Thr Val Ser
        180                 185                 190

Gly Asn His Gln Ile Val Ser Gly Ser His Ser Thr Val Ser Gly Asn
        195                 200                 205

His Asn Thr Val Ser Gly Arg Asn Asn Ser Val Tyr Gly Asn Asn Asn
210                 215                 220

Ile Val Ser Gly Ser Asn His Val Val Tyr Gly Asn Asn Lys Val Val
225                 230                 235                 240

Thr Gly Gly

<210> SEQ ID NO 14
<211> LENGTH: 243
<212> TYPE: PRT
<213> ORGANISM: Festuca arundinacea

<400> SEQUENCE: 14

Met Ala Lys Cys Trp Gln Leu Leu Phe Leu Ala Phe Leu Leu Pro
1               5                   10                  15

Ala Ala Ser Ala Ala Ser Arg His Pro Asp Asp Leu Arg Ala Leu Gln
                20                  25                  30

Asp Phe Ala Gly Asn Leu Arg Gly Gly Val Val Leu Arg Ala Ala
            35                  40                  45

Leu Ser Gly Gly Ser Cys Cys Asp Trp Glu Gly Ala Gly Cys Asp Gly
    50                  55                  60

Ala Ser Gly Arg Val Thr Ser Phe Gln Ile Leu Leu Lys Gly Leu Thr
65                  70                  75                  80

Thr Ala Gly Arg Ser Leu Gly Lys Ala Phe Thr Asn Met Pro Leu His
                85                  90                  95

Val Lys Ser Ser Gln Gly Thr Leu Asp Glu Glu His Asn Thr Ile Thr
            100                 105                 110

Gly Ile Asn Asn Thr Val Lys Ser Gly Ser Asn Asn Val Val Ser Gly
            115                 120                 125

Asn Asp Asn Thr Val Ile Ser Gly Asn Asn Val Val Ser Gly Ser
    130                 135                 140

His Asn Thr Val Val Phe Gly Gly Asp Asn Phe Leu Ser Gly Ser Asn
145                 150                 155                 160

His Val Val Ser Gly Asn His Val Val Thr Asp Asn Lys Asn Ala
                165                 170                 175

Val Ser Gly Asp His Asn Thr Val Ser Gly Ser Gln Asn Thr Val Ser
        180                 185                 190

Gly Asn His His Ile Ile Ser Ala Ser His Ser Thr Ile Ser Gly Asn
        195                 200                 205

His Asn Thr Val Ser Gly Ser Asn Asn Phe Val Ser Gly Asn Asn Asn
210                 215                 220
```

-continued

```
Ile Val Ser Gly Ser Asn His Val Val Tyr Gly Asn Asn Lys Val Val
225                 230                 235                 240

Thr Gly Gly

<210> SEQ ID NO 15
<211> LENGTH: 267
<212> TYPE: PRT
<213> ORGANISM: Lolium perenne

<400> SEQUENCE: 15

Met Pro Glu Tyr Met Ala Lys Cys Cys Met Leu Leu Val Phe Leu Gly
 1               5                  10                  15

Phe Ile Leu Gln Val Ala Gly Ala Thr Ser Trp Ser Cys His His Asp
            20                  25                  30

Asp Leu His Ala Leu Arg Gly Leu Ala Glu Asn Leu Ser Gly Lys Gly
        35                  40                  45

Ala Val Arg Leu Arg Ala Ala Trp Ser Gly Ala Ser Cys Cys Ser Trp
    50                  55                  60

Glu Gly Val Gly Cys Glu Thr Ala Ser Gly Arg Val Val Ala Leu Arg
65                  70                  75                  80

Leu Pro Lys Arg Gly Leu Gly Gly Ile Ile Pro Ser Ile Gly Glu
                85                  90                  95

Leu Asp His Leu Arg Tyr Leu Asp Leu Ser Gly Asn Ser Leu Val Gly
            100                 105                 110

Glu Val Pro Lys Ser Leu Gln Ile Arg Leu Lys Ser Leu Thr Thr Asp
        115                 120                 125

Ser Gln Ser Leu Gly Met Gly Ser Ile Asn Met Leu Leu His Val Ser
    130                 135                 140

Ser Arg Arg Thr Leu Asp Glu Glu Pro Asn Thr Ile Ser Gly Thr Asn
145                 150                 155                 160

Asn Ser Val Gly Ser Gly Ser Asn Asn Val Val Ser Gly Asn Asp Asn
                165                 170                 175

Thr Val Val Ser Gly Asn Asn Asn His Val Ser Gly Ser Asn Asn Thr
            180                 185                 190

Val Val Thr Gly Ser Asp Asn Thr Val Val Gly Ser Asn His Val Val
        195                 200                 205

Ser Gly Thr Lys His Ile Val Thr Asp Asn Asn Val Val Ser Gly
    210                 215                 220

Asn Asp Asn Asn Val Ser Gly Ser Phe His Thr Val Ser Gly Glu His
225                 230                 235                 240

Asn Thr Val Ser Gly Ser Asn Asn Thr Val Ser Gly Ser Asn His Ile
                245                 250                 255

Val Ser Gly Ser Asn Lys Val Val Thr Asp Gly
            260                 265

<210> SEQ ID NO 16
<211> LENGTH: 269
<212> TYPE: PRT
<213> ORGANISM: Festuca arundinacea
<220> FEATURE:
<221> NAME/KEY: VARIANT
<222> LOCATION: (1)...(269)
<223> OTHER INFORMATION: Xaa = Any Amino Acid
```

```
<400> SEQUENCE: 16

Met Pro Glu Tyr Met Ala Lys Cys Cys Met Leu Leu Leu Leu Leu Ala
 1               5                  10                  15

Phe Ile Leu Leu Gln Val Ala Gly Ala Thr Ser Trp Ser Cys His His
             20                  25                  30

Asp Asp Leu Arg Ala Leu Arg Gly Phe Ala Glu Asn Leu Ser Gly Lys
             35                  40                  45

Gly Ala Val Arg Leu Arg Ala Ala Trp Ser Gly Ala Ser Cys Cys Ser
 50                  55                  60

Trp Glu Gly Val Gly Cys Glu Thr Ala Ser Gly Arg Val Ala Ala Leu
 65                  70                  75                  80

Arg Leu Pro Lys Arg Gly Leu Gly Gly Thr Ile Pro Ser Ser Ile Gly
             85                  90                  95

Glu Leu Asp His Leu Arg Cys Leu Asp Leu Ser Gly Asn Ser Leu Val
            100                 105                 110

Gly Lys Val Pro Lys Ser Leu Gln Ile Arg Leu Xaa Ser Leu Ser Thr
            115                 120                 125

Asp Gly Gln Ser Leu Gly Met Gly Ser Ile Asn Thr Leu Leu His Val
130                 135                 140

Ser Ser Asn Arg Arg Thr Leu Asp Glu Glu Pro Asn Thr Ile Ser Gly
145                 150                 155                 160

Thr Asn Asn Ser Val Gly Ser Gly Ser Asn Asn Val Val Ser Gly Asn
            165                 170                 175

Asp Asn Thr Val Ile Ser Gly Asn Asn Asn His Val Ser Gly Ser Asn
            180                 185                 190

Asn Thr Val Val Thr Gly Ser Asp Asn Thr Leu Val Gly Ser Asn His
            195                 200                 205

Val Val Ser Gly Thr Lys His Ile Val Thr Asp Asn Asn Val Val
210                 215                 220

Ser Gly Asn Asp Asn Asn Val Ser Gly Ser Phe His Thr Val Ser Gly
225                 230                 235                 240

Glu His Asn Thr Val Ser Gly Ser Asn Asn Thr Val Ser Gly Ser Asn
            245                 250                 255

His Val Val Ser Gly Ser Asn Lys Val Val Thr Asp Gly
            260                 265

<210> SEQ ID NO 17
<211> LENGTH: 281
<212> TYPE: PRT
<213> ORGANISM: Lolium perenne

<400> SEQUENCE: 17

Met Ala Lys Cys Trp Leu Leu Leu Phe Leu Val Phe Leu Leu Leu
 1               5                  10                  15

Ala Met Ser Ala Thr Ser Cys His Leu Asp Asp Leu Arg Ala Leu Arg
             20                  25                  30

Gly Phe Val Gly Asn Leu Asn Gly Gly Ala Leu Leu Arg Gly Thr
             35                  40                  45

Trp Ser Gly Ser Ser Cys Cys Asp Trp Glu Gly Val Gly Cys Asp Gly
 50                  55                  60

Thr Ser Gly Arg Val Thr Ala Leu Arg Leu Pro Ile Ser Leu Glu Asp
 65                  70                  75                  80

Cys Gly Lys Leu Lys Ser Leu Asn Leu Ala Asn Glu Arg Leu Val Gly
             85                  90                  95
```

```
Thr Ile Pro Ser Trp Ile Gly Glu Leu Asp His His Cys Tyr Leu Val
                100                 105                 110

Leu Ser Asp Asn Ser Leu Val Gly Lys Ala Pro Asn Ser Leu His Asn
            115                 120                 125

Ser Leu Gln Ile Arg Leu Lys Gly Leu Ala Thr Ala Gly Arg Ser Leu
        130                 135                 140

Gly Met Ala Phe Ala Asn Met Pro Leu His Val Lys Gly Asn Arg Arg
145                 150                 155                 160

Thr Leu Asp Glu Gln Thr Asn Thr Ile His Gly Thr Asn Asn Thr Val
                165                 170                 175

Arg Ser Gly Asn Asp Asn Ala Val Ser Gly Asn Asp Asn Thr Val Ile
            180                 185                 190

Cys Gly Asn Asn Asn Thr Val Ser Gly Ser Asn Asn Thr Ile Ala Ser
        195                 200                 205

Gly Ser Asp Asn Ile Val Thr Gly Ser Asn His Ile Val Cys Gly Thr
210                 215                 220

Lys His Ile Ile Thr Asp Asn Asn Asn Asp Val Ser Gly Asn Asp Asn
225                 230                 235                 240

Asn Val Ser Gly Ser Phe His Thr Val Ser Gly Ser His Asn Thr Val
                245                 250                 255

Ser Gly Ser Asn Asn Thr Val Ser Gly Ser Asn His Val Val Ser Gly
            260                 265                 270

Ser Asn Lys Leu Val Thr Gly Asp Glu
        275                 280

<210> SEQ ID NO 18
<211> LENGTH: 277
<212> TYPE: PRT
<213> ORGANISM: Festuca arundinacea

<400> SEQUENCE: 18

Met Ala Lys Cys Trp Leu Leu Leu Phe Leu Val Val Leu Leu Pro
  1               5                  10                  15

Ala Ala Ser Ala Thr Ser Cys His Pro Asp Asp Leu Arg Ala Leu Arg
            20                  25                  30

Gly Phe Val Gly Asn Leu Asn Gly Gly Val Leu Leu His Gly Ala
        35                  40                  45

Trp Ser Gly Ser Leu Cys Cys Ala Trp Glu Gly Gly Cys Asp Gly
  50                  55                  60

Thr Ser Gly Arg Val Thr Ala Leu Arg Leu Pro Ile Ser Leu Lys Asp
 65                  70                  75                  80

Cys Gly Lys Leu Lys Ser Leu Asn Leu Ala Asn Asp Arg Leu Val Gly
                85                  90                  95

Thr Ile Pro Ser Trp Ile Gly Glu Leu Asp His Leu Cys Tyr Leu Val
                100                 105                 110

Leu Ser Asp Asn Ser Leu Val Gly Lys Val Pro Asn Ser Leu Gln Ile
            115                 120                 125

Arg Leu Lys Gly Leu Ala Thr Ala Gly Arg Ser Leu Gly Met Ala Phe
        130                 135                 140

Ala Asn Met Pro Leu His Val Lys Gly Asn Arg Arg Thr Leu Asp Glu
145                 150                 155                 160

Gln Thr Asn Thr Ile Gln Gly Thr Asn Asn Thr Val Arg Ser Gly Asn
                165                 170                 175

Asp Asn Ala Val Ser Gly Asn Asp Asn Thr Val Ile Cys Gly Asn Asn
            180                 185                 190
```

Asn Thr Val Ser Gly Ser Asn Thr Ile Ser Gly Ser Asp Asn
         195                 200                 205

Ile Val Thr Gly Ser Asn Gln Val Val Cys Gly Thr Lys His Ile Ile
         210                 215                 220

Thr Asp Asn Asn Asn Asp Val Ser Gly Asn Asp Asn Asn Val Ser Gly
225                 230                 235                 240

Ser Ser His Thr Val Ser Gly Ser His Asn Thr Val Ser Gly Ser Asn
             245                 250                 255

Asn Thr Val Ser Gly Ser Asn His Val Val Ser Gly Ser Asn Lys Val
             260                 265                 270

Val Thr Gly Asp Glu
         275

<210> SEQ ID NO 19
<211> LENGTH: 277
<212> TYPE: PRT
<213> ORGANISM: Lolium perenne

<400> SEQUENCE: 19

Met Ala Lys Cys Trp Leu Leu Leu Phe Leu Val Phe Leu Leu Leu
1               5                   10                  15

Ala Val Cys Ala Thr Ser Cys His Pro Asp Asp Leu Arg Ala Leu Arg
             20                  25                  30

Gly Phe Val Gly Asn Leu Asn Gly Gly Val Leu Leu Arg Glu Thr
             35                  40                  45

Trp Ser Gly Ser Ser Cys Cys Ala Trp Glu Gly Val Gly Cys Asp Gly
     50                  55                  60

Thr Ser Gly Arg Val Thr Ala Leu Arg Leu Pro Ile Ser Leu Glu Asp
65                  70                  75                  80

Cys Gly Lys Leu Lys Ser Leu Asn Leu Ala Asn Glu Arg Leu Val Gly
                 85                  90                  95

Thr Ile Pro Ser Trp Ile Gly Glu Leu Asp His His Cys Tyr Phe Val
             100                 105                 110

Leu Ser Asp Asn Ser Leu Val Gly Lys Val Pro Asn Ser Leu Gln Ile
         115                 120                 125

Arg Leu Lys Gly Leu Ala Thr Ala Gly Arg Ser Leu Gly Met Ala Phe
     130                 135                 140

Ala Asn Met Pro Leu His Val Lys Gly Asn Arg Arg Thr Leu Asp Glu
145                 150                 155                 160

Gln Thr Asn Thr Ile His Gly Thr Asn Asn Thr Val Arg Ser Gly Asn
                 165                 170                 175

Asp Asn Ala Val Ser Gly Asn Asp Asn Thr Val Met Cys Gly Asn Asn
             180                 185                 190

Asn Thr Val Ser Gly Ser Asn Thr Ile Ser Ser Gly Ser Asp Asn
         195                 200                 205

Ile Val Thr Gly Ser Asn His Ile Val Cys Gly Thr Lys His Ile Ile
     210                 215                 220

Thr Asp Asn Asn Asn Asp Val Ser Gly Asn Asp Asn Asn Val Ser Gly
225                 230                 235                 240

Ser Phe His Thr Val Ser Gly Ser His Asn Thr Val Ser Gly Ser Asn
             245                 250                 255

Asn Thr Val Ser Gly Ser Asn His Val Val Ser Gly Ser Asn Lys Val
             260                 265                 270

Val Thr Gly Asp Glu
         275

```
<210> SEQ ID NO 20
<211> LENGTH: 280
<212> TYPE: PRT
<213> ORGANISM: Lolium perenne

<400> SEQUENCE: 20

Met Gly Leu Leu Leu Leu Phe Leu Ala Phe Leu Leu Pro Val Ala Cys
1               5                   10                  15

Ala Ala Thr Ser Ser Cys His Pro Asp Asp Leu Arg Ala Leu Arg Gly
            20                  25                  30

Phe Ala Lys Asn Leu Gly Gly Gly Val Leu Leu Arg Thr Ala Trp
        35                  40                  45

Ser Gly Thr Ser Cys Cys Val Trp Glu Gly Val Gly Cys Asn Gly Ala
50                  55                  60

Ser Gly Arg Val Thr Thr Leu Trp Leu Pro Arg Arg Gly Leu Ala Gly
65                  70                  75                  80

Thr Ile Thr Gly Ala Ser Leu Ala Gly Leu Ala Arg Leu Glu Ser Leu
                85                  90                  95

Asn Leu Ala Asn Asn Arg Leu Val Gly Thr Ile Pro Ser Trp Ile Gly
            100                 105                 110

Glu Leu Asp His Leu Leu Tyr Leu Asp Leu Ser His Asn Ser Leu Val
        115                 120                 125

Gly Glu Leu Pro Asn Leu Lys Gly Leu Thr Thr Thr Gly His Leu Leu
130                 135                 140

Gly Met Ala Phe Thr Ser Met Pro Leu Asp Val Lys Pro Asn Arg Arg
145                 150                 155                 160

Thr Leu Ala Val Gln Pro Asn Thr Ile Ser Gly Thr Asn Asn Ser Val
                165                 170                 175

Leu Ser Gly Arg Asn Asn Thr Val Ser Gly Asn Asp Asn Thr Val Ile
            180                 185                 190

Ser Gly Asn Asn Asn Thr Val Ser Gly Ser Phe Asn Thr Val Val Thr
        195                 200                 205

Gly Ser Asp Asn Val Leu Thr Gly Ser Asn His Val Val Ser Gly Arg
210                 215                 220

Asn His Ile Val Thr Asp Asn Asn Ala Val Ser Gly Asp Asp Asn
225                 230                 235                 240

Asn Val Ser Gly Ser Phe His Lys Val Ser Gly Ser His Asn Thr Val
                245                 250                 255

Ser Gly Ser Asn Asn Thr Val Ser Gly Arg Asn His Val Val Ser Gly
            260                 265                 270

Ser Asn Lys Val Val Thr Gly Gly
        275                 280

<210> SEQ ID NO 21
<211> LENGTH: 285
<212> TYPE: PRT
<213> ORGANISM: Festuca arundinacea

<400> SEQUENCE: 21

Met Gly Leu Leu Leu Leu Phe Leu Gly Phe Leu Leu Pro Ala Ala Cys
1               5                   10                  15

Ala Ala Thr Ser Ser Cys His Pro Asp Asp Leu Arg Ala Leu Arg Gly
            20                  25                  30

Phe Ala Lys Asn Val Gly Gly Gly Val Leu Leu Arg Thr Ala Trp
        35                  40                  45

Ser Gly Thr Ser Cys Cys Val Trp Glu Gly Val Gly Cys Asn Gly Ala
50                  55                  60
```

Ser Gly Arg Ile Thr Thr Leu Trp Leu Pro Arg Gly Leu Ala Gly
65                  70                  75                  80

Thr Ile Thr Gly Ala Ser Leu Ala Gly Leu Ala Arg Leu Glu Ser Leu
            85                  90                  95

Asn Leu Ala Asn Asn Arg Leu Val Gly Thr Ile Pro Ser Trp Ile Gly
            100                 105                 110

Glu Leu Asp His Leu Leu Tyr Leu Asp Leu Ser His Asn Ser Leu Val
            115                 120                 125

Gly Glu Leu Pro Asn Arg Leu Gln Ile Arg Leu Lys Gly Leu Thr Thr
130                 135                 140

Thr Gly His Leu Leu Gly Met Ala Phe Thr Asn Met Pro Leu Asp Val
145                 150                 155                 160

Lys Arg Asn Arg Arg Thr Leu Ala Ile Gln Pro Asn Thr Ile Ser Gly
            165                 170                 175

Thr Asn Asn Leu Val Leu Ser Gly Arg Asn Asn Val Val Ser Gly Asn
            180                 185                 190

Asp Asn Thr Val Ile Ser Glu Asn Asn Thr Val Ser Gly Ser Phe
            195                 200                 205

Asn Thr Val Ile Thr Gly Ser Asp Asn Val Leu Thr Gly Ser Asn His
210                 215                 220

Val Val Ser Gly Arg Ser His Ile Val Thr Asp Asn Asn Ser Val
225                 230                 235                 240

Ser Gly Asp Asp Asn Asn Val Ser Gly Ser Phe His Lys Val Ser Gly
            245                 250                 255

Ser His Asn Thr Val Ser Gly Ser Asn Asn Thr Val Ser Gly Arg Asn
            260                 265                 270

His Val Val Ser Gly Ser Asn Lys Ile Val Thr Gly Gly
            275                 280                 285

<210> SEQ ID NO 22
<211> LENGTH: 254
<212> TYPE: PRT
<213> ORGANISM: Lolium perenne

<400> SEQUENCE: 22

Met Ala Lys Cys Leu Met Leu Leu Leu Ser Phe Ala Phe Leu Leu Ser
1               5                   10                  15

Val Ala Gly Thr Ala Thr Ala Thr Pro Cys His Arg Asp Asp Leu Arg
            20                  25                  30

Ala Leu Arg Gly Phe Ala Glu Asn Leu Gly Gly Gly Ala Ile Ser
            35                  40                  45

Leu Arg Ala Ala Trp Ser Gly Ala Ser Cys Cys Asp Trp Glu Gly Val
50                  55                  60

Gly Cys Asp Gly Ala Ser Gly Arg Val Thr Ala Leu Trp Leu Pro Arg
65                  70                  75                  80

Ser Gly Leu Thr Gly Pro Ile Pro Ser Trp Ile Cys Gln Leu His His
            85                  90                  95

Leu Arg Tyr Leu Asp Leu Ser Gly Asn Ala Leu Val Gly Glu Val Pro
            100                 105                 110

Lys Asn Leu Gln Val Gln Leu Lys Gly Ile Thr Asn Met Pro Leu His
            115                 120                 125

Val Met Arg Asn Arg Arg Ser Leu Asp Glu Gln Pro Asn Thr Ile Ser
130                 135                 140

Gly Ser Asn Asn Thr Val Arg Ser Gly Ser Lys Asn Val Leu Ala Gly
145                 150                 155                 160

```
Asn Asp Asn Thr Val Ile Ser Gly Asp Asn Asn Ser Val Ser Gly Ser
            165                 170                 175

Asn Asn Thr Val Val Ser Gly Asn Asp Asn Thr Val Thr Gly Ser Asn
            180                 185                 190

His Val Val Ser Gly Thr Asn His Ile Val Thr Asp Asn Asn Asn Asn
            195                 200                 205

Val Ser Gly Asn Asp Asn Asn Val Ser Gly Ser Phe His Thr Val Ser
            210                 215                 220

Gly Gly His Asn Thr Val Ser Gly Ser Asn Asn Thr Val Ser Gly Ser
225                 230                 235                 240

Asn His Val Val Ser Gly Ser Asn Lys Val Val Thr Asp Ala
            245                 250

<210> SEQ ID NO 23
<211> LENGTH: 262
<212> TYPE: PRT
<213> ORGANISM: Festuca arundinacea

<400> SEQUENCE: 23

Met Ala Lys Cys Leu Met Leu Leu Leu Ser Phe Ala Phe Leu Leu Ser
 1               5                  10                  15

Ala Ala Gly Thr Ala Thr Ala Thr Pro Cys His Arg Asp Asp Leu Arg
            20                  25                  30

Ala Leu Arg Gly Phe Ala Glu Asn Leu Gly Gly Gly Ala Leu Ser
        35                  40                  45

Leu Arg Ala Ala Trp Ser Gly Ala Ser Cys Cys Asp Trp Glu Gly Val
 50                  55                  60

Gly Cys Asp Gly Ala Ser Gly Arg Val Thr Ala Leu Trp Leu Pro Arg
65                   70                  75                  80

Ser Gly Leu Thr Gly Pro Ile Pro Ser Trp Ile Cys Gln Leu His His
                85                  90                  95

Leu Arg Tyr Leu Asp Leu Ser Gly Asn Ala Leu Val Gly Glu Val Pro
            100                 105                 110

Lys Asn Leu Gln Val Gln Leu Lys Gly Leu Thr Ala Ala Gly Arg Ser
            115                 120                 125

Gly Phe Thr Asn Met Pro Leu His Val Met Arg Asn Arg Arg Ser Leu
130                 135                 140

Asp Glu Gln Pro Asn Thr Ile Ser Gly Ser Asn Asn Thr Val Arg Ser
145                 150                 155                 160

Gly Ser Lys Asn Val Val Ala Gly Asn Asp Asn Thr Val Ile Ser Gly
            165                 170                 175

Asp Asn Asn Ser Val Ser Gly Ser Asn Asn Thr Val Val Ser Gly Ser
            180                 185                 190

Asp Asn Thr Val Thr Gly Ser Asn His Val Val Ser Gly Thr Asn His
            195                 200                 205

Ile Val Thr Asp Asn Asn Asn Asn Val Ser Gly Asn Asp Asn Asn Val
            210                 215                 220

Ser Gly Ser Phe His Thr Val Ser Gly Gly His Asn Thr Val Ser Gly
225                 230                 235                 240

Ser Asn Asn Thr Val Ser Gly Ser Asn His Val Val Ser Gly Ser Asn
            245                 250                 255

Lys Val Val Thr Asp Ala
            260
```

<210> SEQ ID NO 24
<211> LENGTH: 256
<212> TYPE: PRT
<213> ORGANISM: Lolium perenne

<400> SEQUENCE: 24

```
Met Ala Lys Cys Leu Met Leu Leu Leu Ser Phe Ala Phe Leu Leu Ser
 1               5                  10                  15
Ala Ala Gly Thr Ala Thr Ala Thr Ala Thr Pro Cys His Arg Asp Asp
            20                  25                  30
Leu Arg Ala Leu Arg Gly Phe Ala Glu Asn Leu Gly Gly Gly Gly Ala
        35                  40                  45
Leu Ser Leu Arg Ala Ala Trp Ser Gly Ala Ser Cys Cys Asp Trp Glu
    50                  55                  60
Gly Val Gly Cys Asp Gly Ala Ser Gly Arg Val Thr Ala Leu Trp Leu
65                  70                  75                  80
Pro Arg Ser Gly Leu Thr Gly Pro Ile Pro Ser Trp Ile Phe Gln Leu
                85                  90                  95
His His Leu Arg Tyr Leu Asp Leu Ser Gly Asn Ala Leu Val Gly Glu
           100                 105                 110
Val Pro Lys Asn Leu Gln Val Gln Leu Lys Gly Ile Thr Asn Met Pro
       115                 120                 125
Leu His Val Met Arg Asn Arg Arg Ser Leu Asp Glu Gln Pro Asn Thr
   130                 135                 140
Ile Ser Gly Ser Asn Asn Thr Val Arg Ser Gly Ser Lys Asn Val Leu
145                 150                 155                 160
Ala Gly Asn Asp Asn Thr Val Ile Ser Gly Asp Asn Ser Val Ser
                165                 170                 175
Gly Ser Asn Asn Thr Val Val Ser Gly Asn Asp Asn Val Thr Gly
           180                 185                 190
Ser Asn His Val Val Ser Gly Thr Asn His Ile Val Thr Asp Asn Asn
       195                 200                 205
Asn Asn Val Ser Gly Asn Asp Asn Val Ser Gly Ser Phe His Thr
   210                 215                 220
Val Ser Gly Gly His Asn Thr Val Ser Gly Ser Asn Asn Thr Val Ser
225                 230                 235                 240
Gly Ser Asn His Val Val Ser Gly Ser Asn Lys Val Val Thr Asp Ala
                245                 250                 255
```

<210> SEQ ID NO 25
<211> LENGTH: 1083
<212> TYPE: DNA
<213> ORGANISM: Lolium perenne

<400> SEQUENCE: 25

```
acttgcattc caaaaaggtt tcttgcatac acgtatttag aacaccagaa cttaatccat      60
ggcgaaatgt tggctgctgc tgctcttctt ggtgttcctc ttgctggcca tgagcgcgac     120
gtcgtgccac ctggatgacc tccgcgcgct gcggggcttt gtcgggaacc tcaatggcgg     180
gggtgccctt ctccgtggaa catggtctgg ctcctcatgc tgcgattggg aaggtgtggg     240
ctgcgatggt acaagcggcc gcgtcacggc gttgcggctt ccgattagcc tcgaggactg     300
cggtaagctc aagtcgctca accttgccaa cgaaagattg ttggcacca tcccgtcgtg      360
gattggtgag cttgaccacc attgctactt ggttctctcg gataattcat tggttggtaa     420
ggcacccaat agtttgcaca atagtttgca gataagactc aagggcctcg ccaccgctgg     480
tcgttcacta ggtatggctt tcgctaacat gccattgcat gtgaagggga accgaagaac     540
```

-continued

```
cctcgacgaa caaacaaata caatacatgg gaccaacaac actgttagat ctgggaacga       600
caatgctgtt tctgggaacg acaacactgt catatgtggg aacaacaaca ctgtgtctgg       660
gagcaacaac accattgcat ctggcagtga caatatcgta actggcagca accatattgt       720
atgtgggacc aaacatatca taactgataa caacaatgac gtatccggca atgataataa       780
tgtatctggg agcttccata ctgtatccgg gagccacaat actgtatctg aagtaacaa        840 cactgtatct ggaagcaacc atgtcgtatc tggaagcaac aaagtcgtga caggagatga       900
atgatttgtc aggggattgc ttccatcttt cctaaaggag ctctcaccct agtccaagtt       960
cggtgcagct cacaatcact tggtagggac aatcgagtta tgtaacttca tggatatagc      1020
atcattctcc ctgtttaaat atactttcct gaaaatatct tacataaatg ctgaaaaaaa      1080
aaa                                                                    1083
```

<210> SEQ ID NO 26
<211> LENGTH: 281
<212> TYPE: PRT
<213> ORGANISM: Lolium perenne

<400> SEQUENCE: 26

```
Met Ala Lys Cys Trp Leu Leu Leu Phe Leu Val Phe Leu Leu Leu
1               5                   10                  15

Ala Met Ser Ala Thr Ser Cys His Leu Asp Asp Leu Arg Ala Leu Arg
            20                  25                  30

Gly Phe Val Gly Asn Leu Asn Gly Gly Ala Leu Leu Arg Gly Thr
        35                  40                  45

Trp Ser Gly Ser Ser Cys Cys Asp Trp Glu Gly Val Gly Cys Asp Gly
    50                  55                  60

Thr Ser Gly Arg Val Thr Ala Leu Arg Leu Pro Ile Ser Leu Glu Asp
65                  70                  75                  80

Cys Gly Lys Leu Lys Ser Leu Asn Leu Ala Asn Glu Arg Leu Val Gly
                85                  90                  95

Thr Ile Pro Ser Trp Ile Gly Glu Leu Asp His His Cys Tyr Leu Val
            100                 105                 110

Leu Ser Asp Asn Ser Leu Val Gly Lys Ala Pro Asn Ser Leu His Asn
        115                 120                 125

Ser Leu Gln Ile Arg Leu Lys Gly Leu Ala Thr Ala Gly Arg Ser Leu
    130                 135                 140

Gly Met Ala Phe Ala Asn Met Pro Leu His Val Lys Gly Asn Arg Arg
145                 150                 155                 160

Thr Leu Asp Glu Gln Thr Asn Thr Ile His Gly Thr Asn Asn Thr Val
                165                 170                 175

Arg Ser Gly Asn Asp Asn Ala Val Ser Gly Asn Asp Asn Thr Val Ile
            180                 185                 190

Cys Gly Asn Asn Asn Thr Val Ser Gly Ser Asn Asn Thr Ile Ala Ser
        195                 200                 205

Gly Ser Asp Asn Ile Val Thr Gly Ser Asn His Ile Val Cys Gly Thr
    210                 215                 220

Lys His Ile Ile Thr Asp Asn Asn Asp Val Ser Gly Asn Asp Asn
225                 230                 235                 240

Asn Val Ser Gly Ser Phe His Thr Val Ser Gly Ser Asn Thr Val
                245                 250                 255
```

```
Ser Gly Ser Asn Asn Thr Val Ser Gly Ser Asn His Val Val Ser Gly
            260                 265                 270

Ser Asn Lys Val Val Thr Gly Asp Glu
        275                 280
```

<210> SEQ ID NO 27
<211> LENGTH: 20
<212> TYPE: DNA
<213> ORGANISM: Artificial Sequence
<220> FEATURE:
<223> OTHER INFORMATION: Made in the lab

<400> SEQUENCE: 27
gaattcggta ccccatcaac                                              20

<210> SEQ ID NO 28
<211> LENGTH: 20
<212> TYPE: DNA
<213> ORGANISM: Artificial Sequence
<220> FEATURE:
<223> OTHER INFORMATION: Made in the lab

<400> SEQUENCE: 28
gcatgtgagt gaacgcctta                                              20

<210> SEQ ID NO 29
<211> LENGTH: 20
<212> TYPE: DNA
<213> ORGANISM: Artificial Sequence
<220> FEATURE:
<223> OTHER INFORMATION: Made in the lab

<400> SEQUENCE: 29
gaattcggta ccccatcaac                                              20

<210> SEQ ID NO 30
<211> LENGTH: 20
<212> TYPE: DNA
<213> ORGANISM: Artificial Sequence
<220> FEATURE:
<223> OTHER INFORMATION: Made in the lab

<400> SEQUENCE: 30
gtgatcaagc tcaccaatcg                                              20

<210> SEQ ID NO 31
<211> LENGTH: 20
<212> TYPE: DNA
<213> ORGANISM: Artificial Sequence
<220> FEATURE:
<223> OTHER INFORMATION: Made in the lab

<400> SEQUENCE: 31
gaattcggta ccccatcaac                                              20

<210> SEQ ID NO 32
<211> LENGTH: 20
<212> TYPE: DNA
<213> ORGANISM: Artificial Sequence
<220> FEATURE:
<223> OTHER INFORMATION: Made in the lab

<400> SEQUENCE: 32
aggatgctcc tgtgatggtc                                              20

```
<210> SEQ ID NO 33
<211> LENGTH: 20
<212> TYPE: DNA
<213> ORGANISM: Artificial Sequence
<220> FEATURE:
<223> OTHER INFORMATION: Made in the lab

<400> SEQUENCE: 33
gaattcggta ccccatcaac                                            20

<210> SEQ ID NO 34
<211> LENGTH: 20
<212> TYPE: DNA
<213> ORGANISM: Artificial Sequence
<220> FEATURE:
<223> OTHER INFORMATION: Made in the lab

<400> SEQUENCE: 34
tggtgaagct gacaaatcca                                            20

<210> SEQ ID NO 35
<211> LENGTH: 25
<212> TYPE: DNA
<213> ORGANISM: Artificial Sequence
<220> FEATURE:
<223> OTHER INFORMATION: Made in the lab

<400> SEQUENCE: 35
gaattcggcg tcgtgccacc ctgat                                      25

<210> SEQ ID NO 36
<211> LENGTH: 33
<212> TYPE: DNA
<213> ORGANISM: Artificial Sequence
<220> FEATURE:
<223> OTHER INFORMATION: Made in the lab

<400> SEQUENCE: 36
tctagaggat ccttaacctc ctgtcacgca ttt                             33

<210> SEQ ID NO 37
<211> LENGTH: 28
<212> TYPE: DNA
<213> ORGANISM: Artificial Sequence
<220> FEATURE:
<223> OTHER INFORMATION: Made in the lab

<400> SEQUENCE: 37
gaattcggac gaagaccaca atacaata                                   28

<210> SEQ ID NO 38
<211> LENGTH: 33
<212> TYPE: DNA
<213> ORGANISM: Artificial Sequence
<220> FEATURE:
<223> OTHER INFORMATION: Made in the lab

<400> SEQUENCE: 38
tctagaggat ccttaacctc ctgtcacgca ttt                             33

<210> SEQ ID NO 39
<211> LENGTH: 22
<212> TYPE: DNA
<213> ORGANISM: Artificial Sequence
<220> FEATURE:
<223> OTHER INFORMATION: Made in the lab
```

```
<400> SEQUENCE: 39
gaattcggca acgtcgtggt cg                                    22

<210> SEQ ID NO 40
<211> LENGTH: 33
<212> TYPE: DNA
<213> ORGANISM: Artificial Sequence
<220> FEATURE:
<223> OTHER INFORMATION: Made in the lab

<400> SEQUENCE: 40
tctagaggat ccttaaccat ctgttacgac ttt                        33

<210> SEQ ID NO 41
<211> LENGTH: 25
<212> TYPE: DNA
<213> ORGANISM: Artificial Sequence
<220> FEATURE:
<223> OTHER INFORMATION: Made in the lab

<400> SEQUENCE: 41
gaattcggcg acgtcgtgcc acctg                                 25

<210> SEQ ID NO 42
<211> LENGTH: 33
<212> TYPE: DNA
<213> ORGANISM: Artificial Sequence
<220> FEATURE:
<223> OTHER INFORMATION: Made in the lab

<400> SEQUENCE: 42
tctagaggat cctcattcat ctcctgtcac gag                        33

<210> SEQ ID NO 43
<211> LENGTH: 22
<212> TYPE: DNA
<213> ORGANISM: Artificial Sequence
<220> FEATURE:
<223> OTHER INFORMATION: Made in the lab

<400> SEQUENCE: 43
gaattcgacg ccatgccacc gc                                    22

<210> SEQ ID NO 44
<211> LENGTH: 33
<212> TYPE: DNA
<213> ORGANISM: Artificial Sequence
<220> FEATURE:
<223> OTHER INFORMATION: Made in the lab

<400> SEQUENCE: 44
tctagaggat ccttaagcgt ctgtcacgac ttt                        33
```